United States Patent [19]
Chen et al.

[11] Patent Number: 5,990,109
[45] Date of Patent: Nov. 23, 1999

[54] HETEROCYCLO-SUBSTITUTED IMIDAZOPYRAZINE PROTEIN TYROSINE KINASE INHIBITORS

[75] Inventors: Ping Chen, Lawrenceville; Derek J. Norris, Trenton, both of N.J.; Joel C. Barrish, Holland, Pa.; Edwin J. Iwanowicz, Cranbury, N.J.

[73] Assignee: Bristol-Myers Squibb Co., New York, N.Y.

[21] Appl. No.: 09/262,525

[22] Filed: Mar. 4, 1999

Related U.S. Application Data

[60] Provisional application No. 60/076,789, Mar. 4, 1998.

[51] Int. Cl.$^6$ .......................... C07D 471/14; A61K 31/50
[52] U.S. Cl. ............................ 514/250; 540/599; 544/61; 544/115; 544/346
[58] Field of Search .............................. 544/346, 61, 115; 514/250; 540/599

[56] References Cited

U.S. PATENT DOCUMENTS

| | | |
|---|---|---|
| 4,160,097 | 7/1979 | Warner et al. |
| 4,172,947 | 10/1979 | Warner et al. |
| 4,191,766 | 3/1980 | Warner et al. |
| 4,191,767 | 3/1980 | Warner et al. |
| 4,197,403 | 4/1980 | Warner et al. |
| 4,198,508 | 4/1980 | Warner et al. |
| 4,200,750 | 4/1980 | Warner et al. |
| 4,225,724 | 9/1980 | Warner et al. |
| 4,229,452 | 10/1980 | Warner et al. |
| 4,236,015 | 11/1980 | Warner et al. |
| 4,317,682 | 3/1982 | Katsura et al. |
| 4,440,929 | 4/1984 | Lee et al. |
| 5,034,530 | 7/1991 | Hansen et al. |
| 5,276,028 | 1/1994 | Hansen. |

FOREIGN PATENT DOCUMENTS

| | | |
|---|---|---|
| 728481 | 8/1996 | European Pat. Off. |
| WO97/19079 | 5/1997 | WIPO. |
| 99/09845 | 3/1999 | WIPO. |
| WO99/10341 | 3/1999 | WIPO. |

OTHER PUBLICATIONS

Bolen, J. B., et al., *FASEB Journal*, "The Src family of tyrosine protein kinases in hemopoietic signal transduction", vol. 6, pp. 3403–3409 (1992).

Chan, A.C., et al., *EMBO Journal*, "Activation of ZAP–70 kinase activity by phosphorylation of tyrosine 493 is required for lymphocyte antigen receptor function", vol. 14, pp. 2499–2508, (1995).

Ihle, J. N., *Seminars in Immunology*, "The Janus protein tyrosine kinases in hematopoietic cytokine", vol.7, pp. 247–254 (1995).

Iwashima, M., et al., *Science*, "Sequential Interactions of the TCR with Two Distinct Cytoplasmic Tyrosine Kinases", vol. 263, pp. 1136–1139 (1994).

Schieven, G. L., et al., *Journal of Biological Chemistry*, "ZAP–70 Tyrosine Kinase, CD45, and T Cell Receptor Involvement in UV–and $H_2O_2$–induced T Cell Signal Transduction", vol. 269, No. 32, pp. 20718–20726 (1994).

Ulrich, A., et al., *Cell*, "Signal Transduction by Receptors with Tyrosine Kinase Activity", vol. 61, pp. 203–212 (1990).

Weiss, A., et al., *Cell*, "Signal Transduction by Lymphocyte Antigen Receptors", vol. 76, pp. 263–274 (1994).

Cooper, J. A., et al., *Journal of Biological Chemistry*, "Phosphorylation Sites in Enolase and Lactate Dehydrogenase Utilized by Tyrosine Protein Kinases in Vivo and In Vitro", vol. 259, No. 12, pp. 7835–7841 (1984).

Davey, D.D., et al. *J.Med. Chem.* "Novel Compounds Possessing Potent cAMP and cGMP Phosphodiesterase Inhibitory Activity. Synthesis and Cardiovascular Effects of a Series of Imidazo[1,2–a]quinoxalinones and Imidazo[1,5–a]quinoxalinones and Their AZA Analogues" vol. 34, pp. 2671–2677 (1991).

U.S. Application Serial No. 09/097,338; "Imidazoquinoxaline Protein Tyrosine Kinase Inhibitors;" Filed Jun. 15, 1998.

U.S. Application Serial No. 09/094,797; "Imidazoquinoxaline Protein Tyrosine Kinase Inhibitors;" Filed Jun. 15, 1998.

*Primary Examiner*—Robert Gerstl
*Attorney, Agent, or Firm*—Audrey F. Sher

[57] ABSTRACT

Novel heterocyclo-substituted imidazopyrazines and salts thereof, pharmaceutical compositions containing such compounds, and methods of using such compounds in the treatment of protein tyrosine kinase-associated disorders such as immunologic disorders.

42 Claims, No Drawings

HETEROCYCLO-SUBSTITUTED IMIDAZOPYRAZINE PROTEIN TYROSINE KINASE INHIBITORS

This application claims priority from provisional U.S. application Ser. No. 60/076,789, filed Mar. 4, 1998, which is incorporated herein by reference in its entirety.

FIELD OF THE INVENTION

The present invention relates to heterocyclo-substituted imidazopyrazines and salts thereof, to methods of using such compounds in treating protein tyrosine kinase-associated disorders such as immunologic disorders, and to pharmaceutical compositions containing such compounds.

BACKGROUND OF THE INVENTION

Protein tyrosine kinase (PTKs) are enzymes which, in conjunction with ATP as a substrate, phosphorylate tyrosine residues in peptides and proteins. These enzymes are key elements in the regulation of cell signaling including cell proliferation and cell differentiation. PTKs comprise, inter alia, receptor tyrosine kinases (RPTKs), including members of the epidermal growth factor kinase family (e.g., HER1 and HER2), platelet derived growth factor (PDGF), and kinases that play a role in angiogenesis (Tie-2 and KDR); and, in addition, non-receptor tyrosine kinases, including members of the Sky, JAK and Src (e.g., Src, Fyn, Lyn, Lck and Blk) families (see Bolen, J. B. Rowley, R. B., Spana, C., and Tsygankov, A. Y., "The src family of tyrosine protein kinases in hemopoietic signal transduction", *FASEB J.*, 6, 3403–3409 (1992); Ulrich, A. and Schlessinger, J., "Signal transduction by receptors with tyrosine kinase activity", *Cell*, 61, 203–212 (1990); and Ihle, J. N., "The Janus protein tyrosine kinases in hematopoetic cytokine signaling", *Sem. Immunol.*, 7, 247–254 (1995)).

Enhanced activity of PTKs has been implicated in a variety of malignant and nonmalignant proliferative diseases. In addition, PTKs play a central role in the regulation of cells of the immune system. PTK inhibitors can thus impact a wide variety of oncologic and immunologic disorders. Such disorders may be ameliorated by selective inhibition of a certain receptor or non-receptor PTK, such as Lck, or due to the homology among PTK classes, by inhibition of more than one PTK by an inhibitor.

A PTK of particular interest is Lck which is found in T cells where it is involved in phosphorylating key protein substrates. It is required for productive antigen receptor signaling and cell activation. In the absence of Lck activity, the T cell receptor (TCR) zeta chain is not phosphorylated, the kinase ZAP-70 is not activated, and $Ca^{2+}$ mobilization essential for T cell activation does not occur (see Weiss, A. and Littman, D. R. "Signal transduction by lymphocyte antigen receptors", *Cell*, 76, 263–274 (1994); Iwashima, M., Irving, B. A., van Oers, N. S. C., Chan, A. C., and Weiss, A., "Sequential interactions of the TCR with two distinct cytoplasmic tyrosine kinases", *Science*, 263, 1136–1139 (1994); and Chan, A. C., Dalton, M., Johnson, R., Kong, G., Wang, T., Thoma, R., and Kurosaki, T., "Activation of ZAP-70 kinase activity by phosphorylation of tyrosine 493 is required for lymphocyte antigen receptor function", *EMBO J.*, 14, 2499–2508 (1995)). Inhibitors of Lck are thus useful in the treatment of T-cell mediated disorders such as chronic diseases with an important T cell component, for example rheumatoid arthritis, multiple sclerosis and lupus, as well as acute diseases where T cells are known to play an essential role, for example acute transplant rejection and delayed-type hypersensitivity (DTH) reactions.

SUMMARY OF THE INVENTION

The present invention provides heterocyclo-substituted imidazopyrazine compounds of the following formula I and salts thereof, for use as protein tyrosine kinase inhibitors:

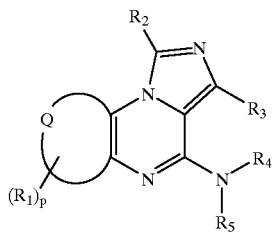

(I)

where
Q, together with the atoms to which it is bonded, forms a 5-, 6- or 7-membered heterocyclic ring;
p is 0 or an integer from 1 to t, where t=3 when Q forms a 5-membered ring, t=4 when Q forms a 6-membered ring, and t=5 when Q forms a 7-membered ring;
each $R_1$, and $R_2$ and $R_3$, are independently selected from:
(1) hydrogen or $R_6$, where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
(2) —OH or —$OR_6$;
(3) —SH or —$SR_6$;
(4) —$C(O)_qH$, —$C(O)_qR_6$, or —O—$C(O)_qR_6$, where q is 1 or 2;
(5) —$SO_3H$ or —$S(O)_qR_6$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$SiR_{13}R_{14}R_{15}$;
(13) —$P(O)(OR_6)_2$;
(14) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(15) any two groups $R_1$ may, together with the atoms to which they are attached, form a heterocyclo group, which group is unsubstituted or substituted with $Z_1$, $Z_2$ and $Z_3$;
$R_4$ and $R_5$:
(1) are each independently hydrogen, $R_6$, or —$C(O)R_6$; or
(2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or (3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
(1) alkyl; or
(2) phenyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —C(O)$_q$H, —C(O)$_q Z_6$, or —O—C(O)$_q Z_6$;
(5) —$SO_3$H or —S(O)$_q Z_6$;
(6) halo;
(7) cyano;
(8) nitro;
(9) —$Z_4$—$NZ_7 Z_8$;
(10) —$Z_4$—N($Z_9$)—$Z_5$—$NZ_7 Z_8$;
(11) —$Z_4$—N($Z_{10}$)—$Z_5$—$Z_6$;
(12) —$Z_4$—N($Z_{10}$)—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—(CH$_2$)$_q$—O—;

$Z_4$ and $Z_5$ are each independently:
(1) a single bond;
(2) —$Z_{11}$—S(O)$_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—; or
(8) —$Z_{11}$—C(O)—O—$Z_{12}$—;

$Z_7$, $Z_8$, $Z_9$ and $Z_{10}$;
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
(1) a single bond;
(2) alkylene;
(3) alkenylene; or
(4) alkynylene.

DETAILED DESCRIPTION OF THE INVENTION

The following are definitions of terms used in this specification. The initial definition provided for a group or term herein applied to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —(CH$_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The terms "ar" or "aryl" refer to phenyl, naphthyl and biphenyl.

The terms "cycloalkyl" and "cycloalkenyl" refer to cyclic hydrocarbon groups of 3 to 8 carbon atoms.

The terms "halogen" and "halo" refer to fluorine, chlorine, bromine and iodine.

The term "unsaturated ring" includes partially unsaturated and aromatic rings.

The terms "heterocycle", "heterocyclic" or "heterocyclo" refer to fully saturated or unsaturated, including aromatic ("heteroaryl") or nonaromatic cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, diazepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl, sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Where q is 1 or 2, "—C(O)$_q$H" denotes —C(O)—H or —C(O)—OH; "—C(O)$_q$R$_6$" or "—C(O)$_q$Z$_6$" denote, respectively, —C(O)—R$_6$ or —C(O)—OR$_6$, or —C(O)—Z$_6$ or —C(O)—OZ$_6$; "—O—C(O)$_q$R$_6$" or "—O—C(O)$_q$Z$_6$" denote, respectively, —O—C(O)—R$_6$ or —O—C(O)—OR$_6$, or —O—C(O)—Z$_6$ or —O—C(O)—OZ$_6$; and "—S(O)$_q$R$_6$" or "—S(O)$_q$Z$_6$" denote, respectively, —SO—R$_6$ or —SO$_2$—R$_6$, or —SO—Z$_6$ or —SO$_2$—Z$_6$.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, aliginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g., methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

In certain instances, compounds of the formula I, and salts thereof, may exist in tautomeric form, for example, the form having the following structure, and salts thereof, where R$_5$ is hydrogen and Q, p, R$_1$, R$_2$, R$_3$ and R$_4$ are as defined above:

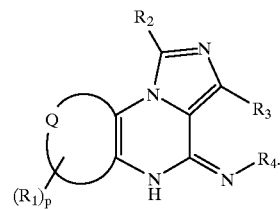

All such tautomers are contemplated herein as part of the present invention.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substituents thereof are chosen to provide stable moieties and compounds.

Preferred Compounds

Preferred compounds of the present invention are compounds of the formula I, and salts thereof, wherein Q, together with the atoms to which it is bonded, form pyridine, pyrimidine, pyrazole or imidazole and wherein one or more, and especially all, of p, R$_1$, R$_2$, R$_3$, R$_4$, and R$_5$ are selected from the following definitions:

p is 0, 1 or 2;

each R$_1$ is independently selected from hydrogen; —OR$_6$; —Z$_4$—NR$_7$R$_8$; —Z$_4$—N(R$_{12}$)—Z$_5$—R$_6$; alkoxy; nitro; halo; or alkyl, aryl or heterocyclo, each of which is unsubstituted or substituted with Z$_1$, Z$_2$ and Z$_3$;

R$_2$ is selected from hydrogen, —Z$_4$—N(R$_9$)—Z$_5$—NR$_{10}$R$_{11}$, or alkyl, where alkyl is unsubstituted or substituted with Z$_1$, Z$_2$ and Z$_3$;

R$_3$ is selected from hydrogen or alkyl;

R$_4$ is phenyl substituted with Z$_1$, Z$_2$ and one or two groups Z$_3$, where said Z$_1$, Z$_2$ and Z$_3$ substituents are selected from hydrogen, halo, lower alkyl, lower alkoxy, —Z$_4$—NZ$_7$Z$_8$, or heterocyclo; and R$_5$ is hydrogen.

Such compounds wherein Q, together with the atoms to which it is bonded, forms pyridine are particularly preferred.

Methods of Preparation

The compounds of the formula I may be prepared by methods such as those illustrated in the following Schemes I to V. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art.

The method described herein may be carried out with starting materials and/or reagents in solution or alternatively, where appropriate, with one or more starting materials or reagents bound to a solid support (see (1) Thompson, L. A., Ellman, J. A., *Chemical Reviews*, 96, 555–600 (1996); (2) Terrett, N. K., Gardner, M., Gordon, D. W., Kobylecki, R. J., Steele, J., *Tetrahedron*, 51 8135–8173 (1995); (3) Gallop, M. A., Barrett, R. W., Dower, W. J., Fodor, S. P. A., Gordon, E. M., *Journal of Medicinal Chemistry*, 37, 1233–1251 (1994); (4) Gordon, E. M., Barrett, R. W., Dower, W. J., Fodor, S. P. A., Gallop, M. A., *Journal of Medicinal Chemistry*, 37, 1385–1401 (1994); (5) Balkenhohl, F., von dem Bussche-Hünnefeld, Lansky, A., Zechel, C., *Angewandte Chemie International Edition in English*, 35, 2288–2337 (1996); (6) Balkenhohl, F., von dem Bussche-Hünnefeld, Lansky, A., Zechel, C., *Angewandte Chemie*, 108, 2436–2487 (1996); and (7) Sofia, M. J., *Drugs Discovery Today*, 1, 27–34 (1996)).

2 in the presence of a base such as sodium, potassium, or cesium carbonate, or an amine base such as triethyl amine, diisopropylethyl amine, 1,8-diazabicyclo[5.4.0]undec-7-ene ("DBU"), or the like, in an appropriate solvent to give the imidazole derivative 3 (Davey, et al., *J. Med. Chem.*, 34, 2671 (1991)). $L_2$ may optionally be absent, where $R_1$ is hydrogen in the final compound I. Also, more than one $L_2$ group may be present on the ring Q where two or more groups $R_1$ are present in the final compound I. The reaction may also be carried out in the presence of a copper I salt such as cuprous chloride, cuprous bromide, or cuprous iodide (Sitkina, et al., *Khim Geterotskil Soed* in 143 (1966); Grimmett, et al., *Aust. J. Chem.*, 32, 2203 (1979); Sugaya, et al., *Synthesis*, 73 (1994)). Preferred leaving groups in 1 (especially, $L_1$) are F and Cl in the absence of a copper I salt and Br and I in the presence of a copper I salt.

The nitro group of 3 may then be reduced to provide the corresponding amine 4 by methods such as those known in the art (e.g., Hudlicky, "Reductions in Organic Chemistry", Wiley (1984)), for example, by catalytic hydrogenation, or by use of $SnCl_2$, $FeCl_3$, sodium dithionite, or the like.

When $R_5$ is hydrogen, the amine 4 may be converted to the urea 7 by treatment with an isocyanate 5. Alternatively, amine 4 may first be reacted with an aryl chloroformate in

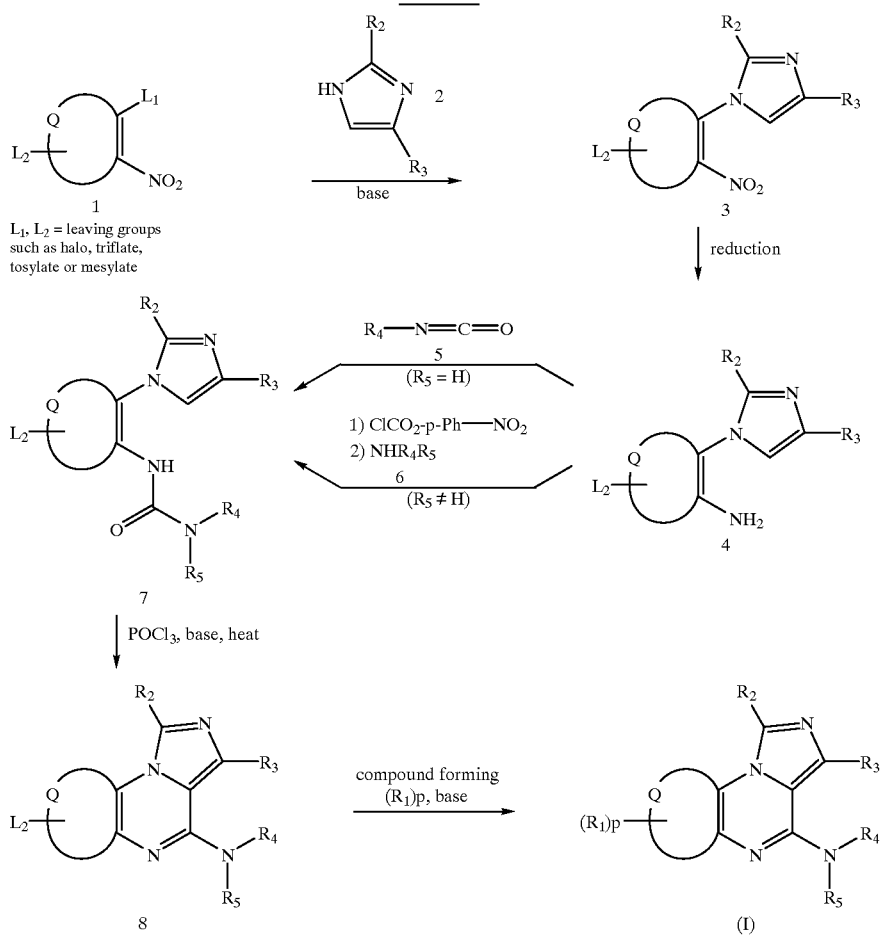

Scheme 1

As shown in Scheme I, an appropriately substituted nitro heterocyclo compound bearing leaving groups $L_1$ and $L_2$ (such as halo) 1 can be reacted with a substituted imidazole the presence of an organic base such as diisopropylethyl amine to give an intermediate aryl carbamate. Treatment of this carbamate with the desired amine 6 provides the urea 7.

Cyclization of the urea 7 to the desired imidazopyrazine 8 may be carried out using phosphorylchloride in the presence of pyridine via a chloroimidate intermediate (U.S. Pat. No. 4,191,766). Reagents other than POCl$_3$ which can also provide a reaction proceeding via the same chloroimidate intermediate (e.g., p-toluenesulfonyl chloride, PCl$_5$, and the like) may be used. Where present, the L$_2$ group of 8 is replaced by R$_1$ to form a compound of the formula I by contact with a compound bearing R$_1$ in the presence of a base.

In the cyclization step, when R$_2$ is hydrogen, 1,2- and 1,5-regioisomers may be formed, wherein the 2- or 5-position carbons of the imidazole ring of 7, respectively, become the bridgehead carbon of the fused imidazole ring of the final products. The 1,5-regioisomer provides the compound of the formula I, and the corresponding 1,2-regioisomer provides the compound having the following formula:

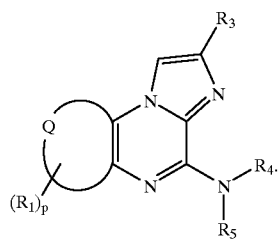

It is preferred to obtain a compound of the formula I substantially free of its corresponding 1,2-regioisomer. The desired 1,5-regioisomer may be separated from the 1,2-isomer by methods such as fractional crystallization, or chromatography on silica gel or C-18.

When R$_2$ and R$_3$ are hydrogen in imidazole 2, preferred R groups may be introduced at later points in the sequence by methods such as those known in the art.

Scheme II

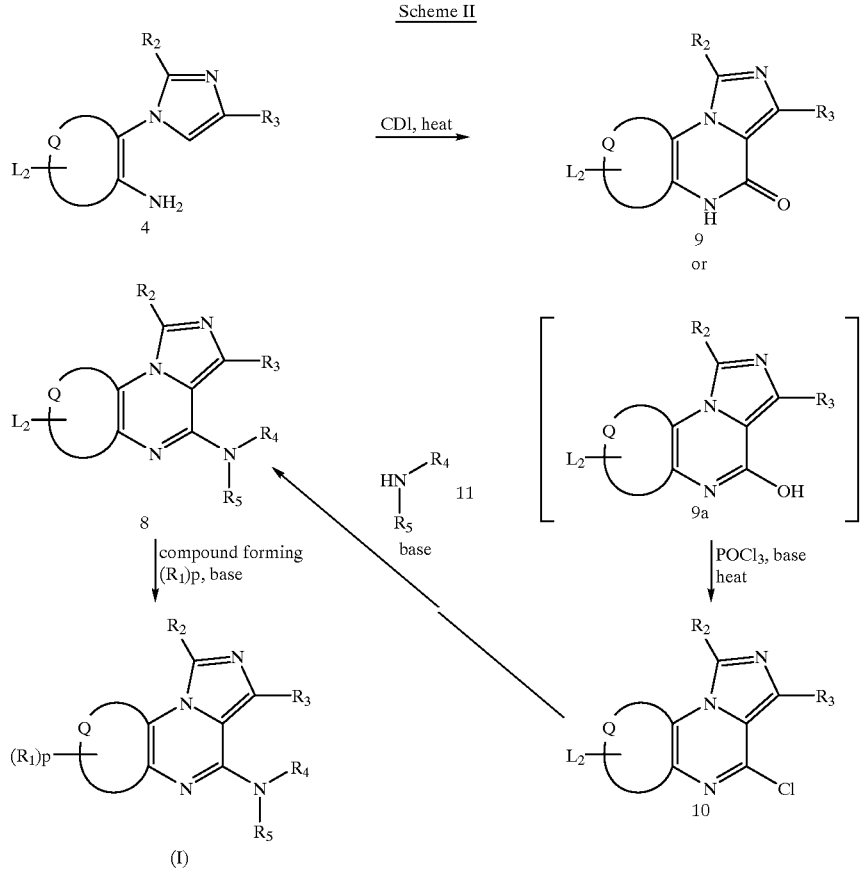

As shown in Scheme II, the aminoimidazole derivative 4 may be reacted with carbonyldiimidazole (CDI) or thiacarbonyldiimidazole, or alternatively phosgene or phosgene equivalents, to give the imidazopyrazine derivative 9 (Davey, et al., *J. Med. Chem.*, 34, 2671 (1991)). Imidazopyrazine derivative 9 may also exist as its tautomer 9a.

When R$_2$ is hydrogen, as in Scheme I, a mixture of regioisomers is possible and the desired 1,5-isomer is preferably separated from the 1,2-isomer by methods such as those described above.

Imidazopyrazine derivative 9 may be converted into its chloroimidate 10 in the presence of phosphorylchloride, or analogous reagents such as SOCl$_2$, PCl$_5$, PPh$_3$/CCl$_4$, or the like, and 10 reacted with the appropriate amine 11, in the presence of a base such as sodium, potassium, or cesium carbonate, or an amine base such as triethylamine, diisopropylethyl amine, DBU, or the like as required, to give compound 8 (Davey, et al., *J. Med. Chem.*, 34, 2671 (1991)).

Compound 8 can be converted to a compound of the formula I as described in Scheme I.
As shown in the following, compound 10 may be converted to thioether 12 by addition of a thiol to 10. Conversion to a compound of formula I may be carried out by addition of an amine 11 in the presence of a mercury II salt such as mercuric chloride or mercuric acetate (Foloppe, et al., *Heterocycles*, 36, 63 (1993)).
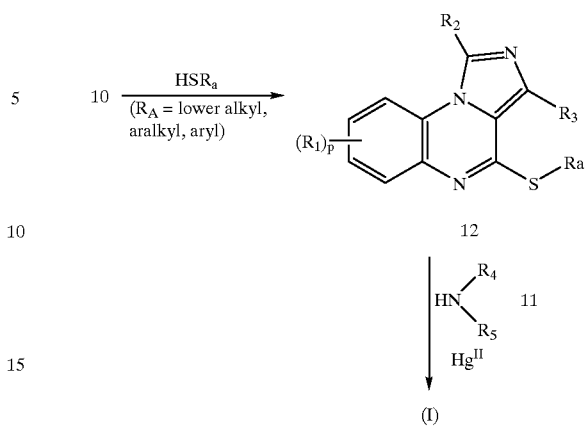
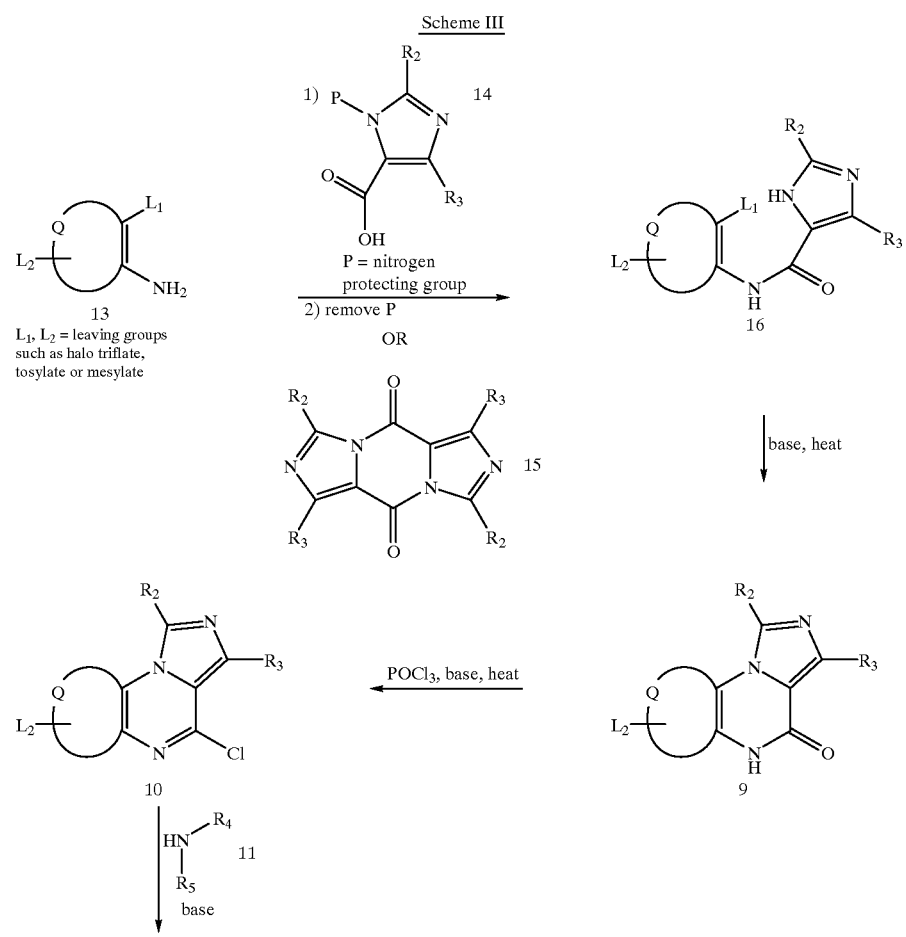

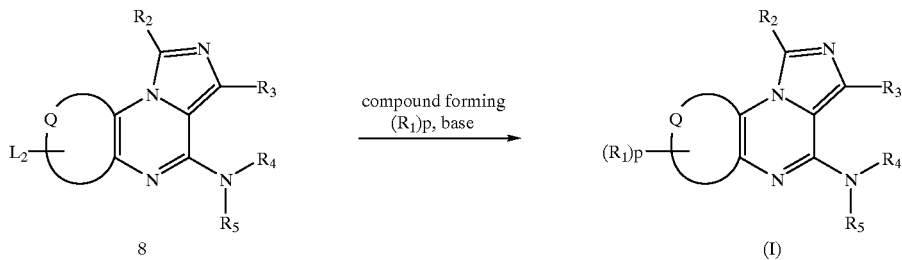

-continued

As shown in Scheme III, an appropriately substituted amino heterocycle 13, where $L_1$ and $L_2$ are as defined above, may be converted to the corresponding amide 16 by either of two methods: 1) direct coupling with the N-protected imidazole carboxylic acid 14 using peptide coupling procedures such as standard methods known in the art (see, for example, Bodanszky, "Principles of peptide synthesis", Springer-Verlag (1984); Bodanszky and Bodansky, "The Practice of Peptide Chemistry", Springer-Verlag (1984)), followed by removal of the nitrogen protecting group P (see, for example, Greene, "Protective Groups in Organic Synthesis", Wiley (1991)); or 2) reaction of 13 with the dimer 15, the latter prepared by methods such as those known in the art (Kasina and Nematollahi, Synthesis, 162 (1975); Godefrol, et al., J. Org. Chem., 29, 3707 (1964)). Exemplary nitrogen protecting groups include carbobenzyloxy or t-butoxycarbonyl. The dimer 15 may also be prepared by coupling the imidazole carboxylic acid:

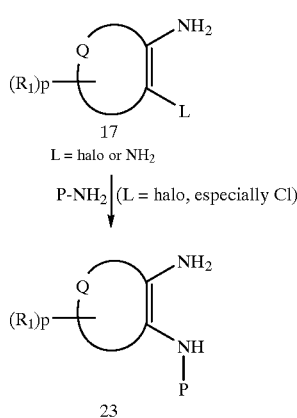

by contacting said acid with thionyl chloride or oxalyl chloride, preferably in the presence of dimethylformamide and heat.

Amide 16 may then be converted to the imidazooxopyrazine 9 by methods analogous to those described for the conversion of 1 to 3 in Scheme I. Conversion of 9 to compound I may then be carried out as described in Scheme II.

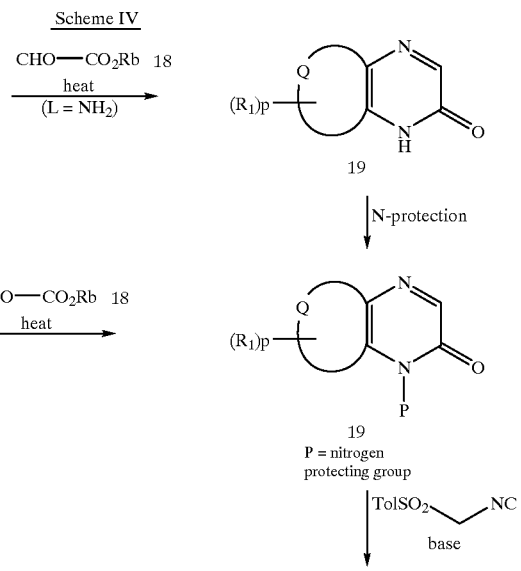

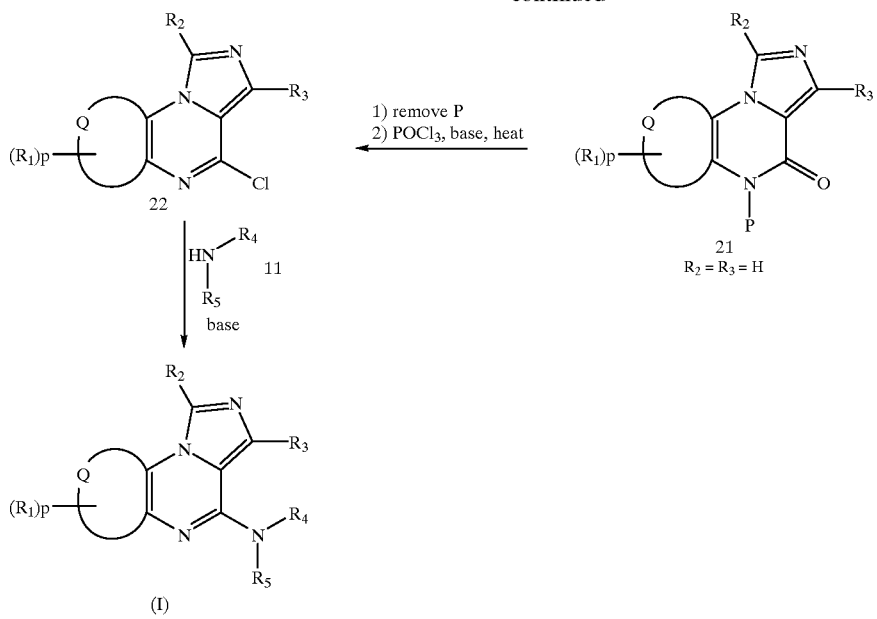

As shown in Scheme IV, the protected heterocyclo-substituted oxopyrazine 20, derived from condensation of diamino heterocycles 17 or 23 with glyoxolate 18(Rb=alkyl, especially methyl or ethyl) may be reacted with tosylmethylisocyanide ("TOSMIC") in the presence of a base such as sodium hydride, n-butyl lithium, lithium, sodium, potassium, or cesium carbonate, or the like, to give the heterocyclo-substituted imidazopyrazine 21(Silvestri, et al., *J. Heterocyclic Chem.*, 31, 1033 (1994); Massa, et al., *J. Heterocyclic Chem.*, 30 749 (1993)). After removal of the nitrogen protecting group P, conversion of 21 to compound I ($R_2$, $R_3$=H) can be carried out by methodology described in Scheme II.

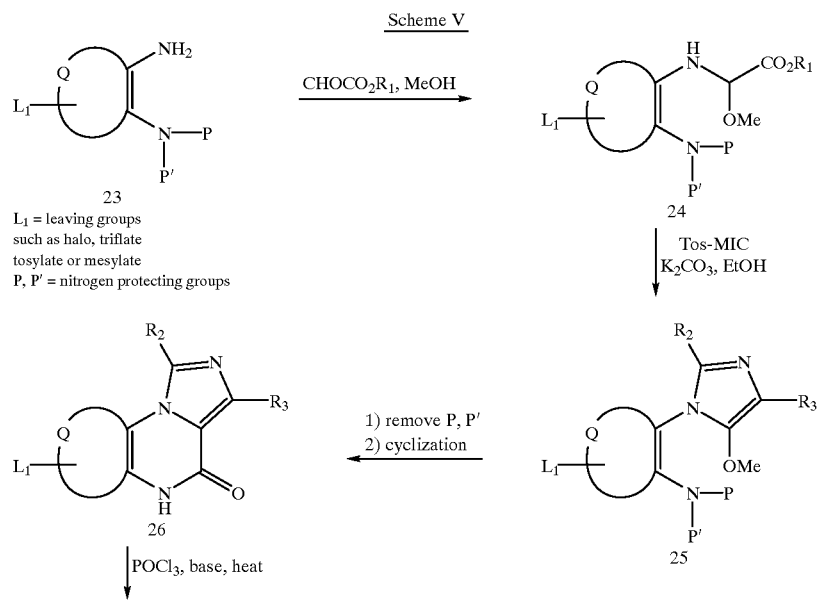

-continued

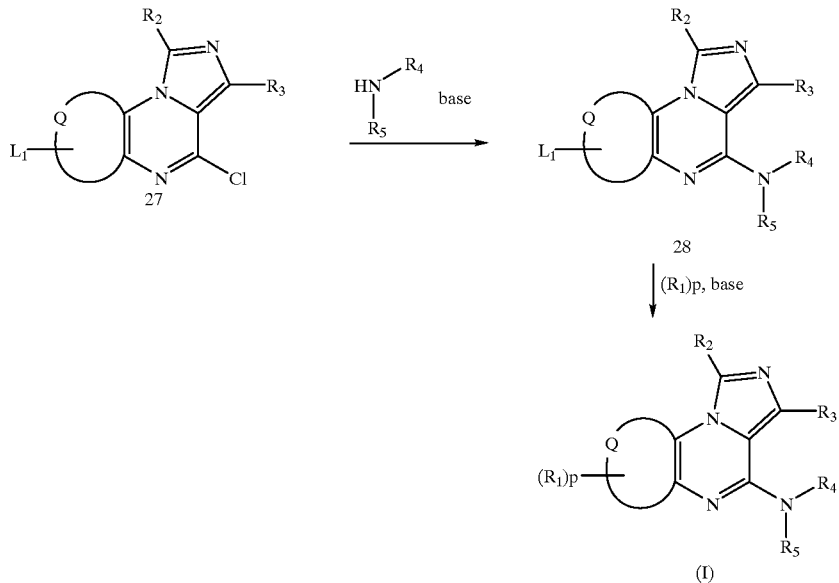

As shown in Scheme V, the appropriately mono-protected and substituted heterocyclic diamine 23 may be reacted with glyoxylate (R1=alkyl, expecially methyl or ethyl) in a alcoholic solvent (such as methanol) to give compound 24. Compound 2 may be reacted with tosylmethylisocyanide ("TOSMIC") in the presence of a base such as sodium hydride, n-butyl lithium, lithium, sodium, potassium, or cesium carbonate, or the like to give the heterocyclo-substituted imidazole 25. Removal of protecting groups of nitrogen, P, P', from 3(P, P' can both be oxygen and in that case, the $NO_2$ group will be reduced by a reducing agent, such as hydrogen, $SnCl_2$, $FeCl_3$, $TiCl_3$, or the like) and cyclization give the heterocyclo-substituted imidazopyrazine 26. Conversion of 26 to compound I can be carried out by methodology described in Scheme II.

Utility

The compounds of the present invention inhibit protein tyrosine kinases, especially Src-family kinases such as Lck, Fyn, Lyn, Src, Yes, Hck, Fgr and Blk, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred embodiment of the present invention. Compounds which selectively block T cell activation and proliferation are preferred. Compounds of the present invention which block the activation of endothelial cell PTK by oxidative stress, thereby limiting surface expression of adhesion molecules that induce neutrophil binding, and which inhibit PTK necessary for neutrophil activation are useful, for example, in the treatment of ischemia and reperfusion injury.

The present invention thus provides methods for the treatment of protein tyrosine kinase-associated disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compounds of the present invention in treating protein tyrosine kinase-associated disorders in exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; chronic obstructive pulmonary disease (COPD), such as emphysema; inflammatory bowel disease, including ulcerative colitis and Chron's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; autoimmune Hypothyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides a method for treating the aforementioned disorders such as atopic dermatitis by administration of any compound capable of inhibiting protein tyrosine kinase.

Src-family kinases other than Lck, such as Hck and Fgr, are important in the Fc gamma receptor induced respiratory burst of neutrophils as well as the Fc gamma receptor responses of monocytes and macrophages. The compounds of the present invention inhibit the Fc gamma induced respiratory burst response in neutrophils, and also inhibit the Fc gamma dependent production of TNF alpha in the monocyte cell line THP-1 that does not express Lck. The ability to inhibit Fc gamma receptor dependent neutrophil, monocyte and macrophage responses results in additional anti-inflammatory activity for the present compounds beyond their effects on T cells. This activity is especially of value, for example, in the treatment of inflammatory diseases such as arthritis or inflammatory bowel disease. In particular, the present compounds are of value for the treatment of autoimmune glomerulonephritis and other instances of glomerulonephritis induced by deposition of immune complexes in the kidney that trigger Fc gamma receptor responses leading to kidney damage. The present compounds also inhibit production of TNF alpha induced by other means, such as, by lipopolysaccharide (LPS). Thus, the compounds are of value for the treatment of toxic shock, septic shock, or other diseases caused by LPS produced by bacterial infection.

In addition, Src family kinases other than Lck, such as Lyn and Src, are important in the Fc epsilon receptor induced degranulation of mast cells and basophils that plays an important role in asthma, allergic rhinitis, and other allergic disease. Fc epsilon receptors are stimulated by IgE-antigen complexes. The compounds of the present invention inhibit the Fc epsilon induced degranulation responses, including in the basophil cell line RBL that does not express Lck. The ability to inhibit Fc epsilon receptor dependent mast cell and basophil responses results in additional anti-inflammatory activity for the present compounds beyond their effect on T cells. In particular, the present compounds are of value for the treatment of asthma, allergic rhinitis, and other instances of allergic disease.

The combined activity of the present compounds towards monocytes, macrophages, T cells, etc. may be of value in the treatment of any of the aforementioned disorders.

In a particular embodiment, the compounds of the present invention are useful for the treatment of the aforementioned exemplary disorders irrespective of their etiology, for example, for the treatment of transplant rejection, rheumatoid arthritis, multiple sclerosis, chronic obstructive pulmonary disease, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The present invention also provides pharmaceutical compositions comprising at least one of the compounds of the formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspension which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to protein tyrosine kinase-associated disorders.

The compounds of the present invention may be employed alone or in combination with each other and/or other suitable therapeutic agents useful in the treatment of protein tyrosine kinase-associated disorders such as PTK inhibitors other than those of the present invention, antiinflammatories, antiproliferatives, chemotherapeutic agents, and immunosuppressants.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CF40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathiprine and cyclophosphamide, TNF-α inhibitors such as tenidap, anti-TNF antibodies or soluble TNF receptor, rapamycin (sirolimus or Rapamune), leflunimide (Arava), and cyclooxygenase-2 (COX-2) inhibitors such as celecoxib (Celebrex) and rofecoxib (Vioxx), or derivatives thereof, and the PTK inhibitors disclosed in the following U.S. patent applications, incorporated herein by reference in their entirety: Ser. No. 60/069,159, filed Dec. 9, 1997 (Attorney Docket No. QA202a*), Ser. No. 60/097,338, filed Jun. 15, 1998 (Attorney Docket No. QA202b), Ser. No. 60/056,797, filed Aug. 25, 1997 (Attorney Docket No. QA205*), Ser. No. 09/094,797, filed Jun. 15, 1998 (Attorney Docket No. QA205a), Ser. No. 60/065,042, filed Nov. 10, 1997 (Attorney Docket No. QA207*), and Ser. No. 09/173,413, filed Oct. 15, 1998, (Attorney Docket No. QA207a). See the following documents Ser. No. 60/056,770, filed Aug. 25, 1999 (Attorney Docket No. QA202*), and references cited therein: Hollenbaugh, D., Douthwright, J., McDonald, V., and Aruffo, A., "Cleavable CD40Ig fusion proteins and the binding to sgp39", J. Immunol. Methods (Netherlands), 188(1), p. 1–7 (Dec. 15, 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", EMBO J (England), 11(12), p 4313–4321 (December 1992); and Moreland, L. W. et al., "Treatment of rheumatoid arthritis with a recombinant human tumor necrosis factor receptor (P75)-Fc fusion protein, New England J. of Medicine, 337(3), p. 141–147(1997).

The above other therapeutic agents, when employed in combination with the compounds of the present invention, may be used, for example, in those amounts indicated in the Physicians' Desk Reference (PDR) or as otherwise determined by one of ordinary skill in the art.

The following assays can be employed in ascertaining the degree of activity of a compound ("test compound") as a PTK inhibitor. Compounds described in the following Examples have been tested in one or more of these assays, and have shown activity.

Enzyme Assay Using Lck, Fyn, Lyn, Hck, Fgr, Src, Blk or Yes

The following assay has been carried out using the protein tyrosine kinases Lck, Fyn, Lyn, Hck, Fgr, Src, Blk and Yes.

The protein tyrosine kinase of interest is incubated in kinase buffer (20 mM MOPS, pH7, 10 mM $MgCl_2$) in the presence of the test compound. The reaction is initiated by the addition of substrates to the final concentration of 1 $\mu$M ATP, 3.3 $\mu$Ci/ml [33P] gamma-ATP, and 0.1 mg/ml acid denatured enolase (prepared as described in Cooper, J. A., Esch, F. S., Taylor, S. S., and Hunter, T., "Phosphorylation sites in enolase and lactate dehydrogenase utilized by tyrosine protein kinases in vivo and in vitro", J. Biol. Chem., 259, 7835–7841 (1984)). The reaction is stopped after 10 minutes by the addition of 10% trichloroacetic acid, 100 mM sodium pyrophosphate followed by 2 mg/ml bovine serum albumin. The labeled enolase protein substrate is precipitated at 4 degrees, harvested onto Packard Unifilter plates and counted in a Topcount scintillation counter to ascertain the protein tyrosine kinase inhibitory activity of the test compound (activity inversely proportional to the amount of labeled enolase protein obtained). The exact concentration of reagents and the amount of label can be varied as needed.

This assay is advantageous as it employs an exogenous substrate (enolase) for more accurate enzyme kinetics, and can be conducted in a 96-well format that is readily automated. In addition, His-tagged protein tyrosine kinases (described below) offer much higher production yields and purity relative to GST-protein tyrosine kinase fusion protein.

The protein tyrosine kinase may be obtained from commercial sources or by recombinant methods described herewith. For the preparation of recombinant Lck, human Lck was prepared as a His-tagged fusion protein using the Life Technologies (Gibco) baculovirus vector pFastBac Hta (commercially available) in insect cells. A cDNA encoding human Lck isolated by PCR (polymerase chain reaction) was inserted into the vector and the protein was expressed using the methods described by the manufacturer. The Lck was purified by affinity chromatography. For the production of Lck in insect cells using baculovirus, see Spana, C., O'Rourke, E. C., Bolen, J. B., and Fargnoli, J., "Analysis of the tyrosine kinase p56lck expressed as a glutathione S-transferase protein in Spodoptera frugiperda cells," Protein expression and purification, Vol. 4, p. 390–397 (1993). Similar methods may be used for the recombinant production of other Src-family kinases.

Cell Assays (1) Cellular Tyrosine Phosphorylation

Jurkat T cells are incubated with the test compound and then stimulated by the addition of antibody to CD3 (monoclonal antibody G19-4). Cells are lysed after 4 minutes or at another desired time by the addition of a lysis buffer containing NP-40 detergent. Phosphorylation of proteins is detected by anti-phosphotyrosine immunoblotting. Detection of phosphorylation of specific proteins of interest such as ZAP-70 is detected by immunoprecipitation with anti-ZAP-70 antibody followed by anti-phosphorylation immunoblotting. Such procedures are described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", J. Biol. Chem., 269, 20718–20726 (1994), and the references incorporated therein. The Lck inhibitors inhibit the tyrosine phosphorylation of cellular proteins induced by anti-CD3 antibodies.

For the preparation of G19-4, see Hansen, J. A., Martin, P. J., Beatty, P. G., Clark, E. A., and Ledbetter, J. A., "Human T lymphocyte cell surface molecules defined by the workshop monoclonal antibodies," in *Leukocyte Typing I,* A. Bernard, J. Boumsell, J. Dausett, C. Milstein, and S. Schlossman, eds. (New York: Springer Verlag), p. 195–212 (1984); and Ledbetter, J. A., June, C. H., Rabinovitch, P. S., Grossman, A., Tsu, T. T., and Imboden, J. B., "Signal transduction through CD4 receptors: stimulatory vs. inhibitory activity is regulated by CD4 proximity to the CD3/T cell receptor", *Eur. J. Immunol.,* 18, 525 (1988).

(2) Calcium Assay

Lck inhibitors block calcium mobilization in T cells stimulated with anti-CD3 antibodies. Cells are loaded with the calcium indicator dye indo-1, treated with anti-CD3 antibody such as the monoclonal antibody G19-4, and calcium mobilization is measured using flow cytometry by recording changes in the blue/violet indo-1 ratio as described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.,* 269, 20718–20726 (1994), and the references incorporated therein.

(3) Proliferation Assays

Lck inhibitors inhibit the proliferation of normal human peripheral blood T cells stimulated to grow with anti-CD3 plus anti-CD28 antibodies. A 96 well plate is coated with a monoclonal antibody to CD3 (such as G19-4), the antibody is allowed to bind, and then the plate is washed. The antibody bound to the plate serves to stimulate the cells. Normal human peripheral blood T cells are added to the wells along with test compound plus anti-CD28 antibody to provide co-stimulation. After a desired period of time (e.g., 3 days), the [3H]-thymidine is added to the cells, and after further incubation to allow incorporation of the label into newly synthesized DNA, the cells are harvested and counted in a scintillation counter to measure cell proliferation.

The following Examples illustrate embodiments of the present invention, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

Abbreviations

DMF=dimethylformamide

EtOAc=ethyl acetate

EtOH=ethanol h=hours

Me=methyl

MeOH=methanol min.=minutes

Pd-C=palladium on carbon

Ph=phenyl

Ret Time=retention time

THF=tetrahydrofuran

EXAMPLE 1

Preparation of N-(2-Chloro-6-methylphenyl)imidazo[1,5-a]pyrido[3,2-e]pyrazin-6-amine

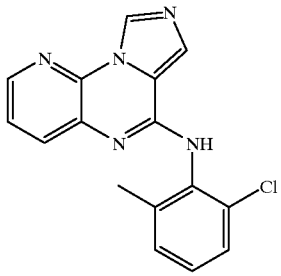

A. N-(2-Chloro-3-pyridinyl)-1H-imidazole-4-carboxamide

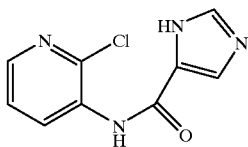

To 3-amino-2-chloropyridine (2.87 g, 22.3 mmol) in THF (13 mL) cooled in a −10° C. bath was added sodium hexamethyldisilazide (51 mL, 51 mmol, 1 M in THF). The mixture was stirred for 1 hr, then a suspension of imidazole carbonyl dimer (2 g, 10.6 mmol, see 15 in Scheme III above) in THF (20 mL) was added and let warm to room temperature. The mixture was stirred for 2 h then quenched with acetic acid. The reaction was concentrated in vacuo followed by the addition of water and saturated sodium bicarbonate. The solid product was collected by filtration with a water and hexane wash, then dried in vacuo to give the desired product 1A.

B. Imidazo[1,5-a]pyrido[3,2-e]pyrazin-6(5H)-one

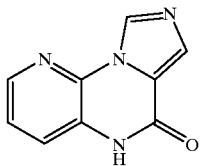

A mixture of 1A (1.89 g, 8.49 mmol) and potassium carbonate (3.5 g, 25.5 mmol) in dimethylacetamide (40 mL) was heated to reflux for 6 h. The reaction mixture was then concentrated in vacuo followed by the addition of water and saturated ammonium chloride. The solid product was collected by filtration with a water wash and then dried in vacuo to give the desired product 1B.

C. 6-Chloroimidazo[1,5-a]pyrido[3,2-e]pyrazine

To 1B (1.37 g, 7.36 mmol) was added phosphorous oxychloride (20 mL) and the mixture was heated to reflux for 12 hr. The reaction was concentrated in vacuo and cooled in an ice bath. Water was added to the residue and neutralized with saturated sodium bicarbonate. The solid product was collected by filtration and purified by column chromatography to yield 1C.

D. N-(2-Chloro-6-methylphenyl)imidazo[1,5-a]pyrido[3,2-e]pyrazin-6-amine

To 2-chloro-6-methylaniline (12.46 mg, 0.088 mmol) in THF (0.4 mL) was added sodium hexamethyldisilazide (0.22 mL, 0.22 mmol, 1 M in THF) and the reaction was heated to reflux for 0.5 h. The reaction was cooled to room temperature and 1C (18 mg, 0.088 mmol) was added in THF (0.8 mL). The mixture was heated to reflux for 0.5 h then cooled to room temperature and quenched with acetic acid. The reaction was concentrated in vacuo followed by addition of water and saturated sodium bicarbonate. The solid product was isolated by filtration with water and hexane rinses, then dried in vacuo to give the desired product 1D. HPLC: 3.255 min (YMC ODS-A C18 S-5 column, 4.6×50 mm, 4 min gradient from 0 to 100% B with 2 min hold at 100% B. Solvent A: 90%$H_2O$-10%MeOH-0.2%$H_3PO_4$; Solvent B: 10%$H_2O$-90%MeOH-0.2% $H_3PO_4$).

EXAMPLES 2 TO 6

The following compounds 2 to 6 (Examples 2 to 6) were prepared from 1C by a route analogous to that used for the preparation of 1D. These compounds have the structure shown below:

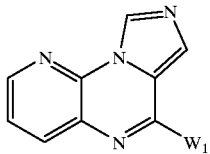

where $W_1$ is defined in the following Table 1. The HPLC retention times of Table 1 were obtained by the method of Example 1. "$X_1$" in Table 1 is not a substituent, but rather shows the point of attachment of $W_1$ to the remainder of the compound of formula I. Unfilled valences on nitrogen indicate the presence of a hydrogen.

TABLE 1

| Ex. No. | $W_1$ | Compound Name | HPLC Ret. time (min) |
|---|---|---|---|
| 2 | (2-bromophenyl)amino group | N-(2-Bromophenyl)imidazo[1,5-a]pyrido[3,2-e]pyrazin-6-amine | 3.524 |
| 3 | (2-chloro-4,6-dimethylphenyl)amino group | N-(2-Chloro-4,6-dimethylphenyl)imidazo[1,5-a]pyrido[3,2-e]pyrazin-6-amine | 3.583 |
| 4 | (4-bromo-2,6-dimethylphenyl)amino group | N-(4-Bromo-2,6-dimethylphenyl)imidazo[1,5-a]pyrido[3,2-e]pyrazin-6-amine | 3.840 |
| 5 | (2,4,6-trimethylphenyl)amino group | N-(2,4,6-Trimethylphenyl)imidazo[1,5-a]pyrido[3,2-e]pyrazin-6-amine | 3.086 |

TABLE 1-continued

| Ex. No. | W₁ | Compound Name | HPLC Ret. time (min) |
|---|---|---|---|
| 6 | 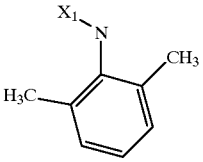 | N-(2,6-Dimethylphenyl)imidazo[1,5-a]pyrido[3,2-e]pyrazin-6-amine | 2.708 |

EXAMPLE 7

Preparation of 2-Chloro-N-(2-chloro-6-methylphenyl)imidazo[1,5-a]pyrido[3,2-e]pyrazin-6-amine

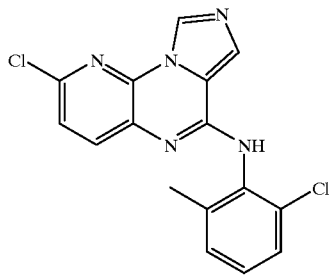

A. N-(2,6-Dichloro-3-pyridinyl)-1H-imidazole-4-carboxamide

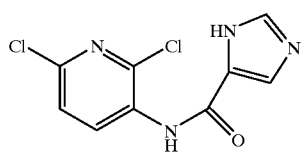

To 3-amino-2,6-dichloropyridine (0.28 g, 1.7 mmol) in THF (1.4 mL) cooled in an ice/MeOH bath was added sodium hexamethyldisilazide (3.4 mL, 3.4 mmol). The mixture was stirred for 0.5 h followed by the addition of imidazole carbonyl dimer (0.16 g, 0.86 mmol) in THF (2 mL). The reaction was warmed to room temperature for 15 min then quenched with acetic acid. The reaction was concentrated in vacuo, then water and saturated sodium bicarbonate was added. The solid product was isolated by filtration with water and hexane rinses, then dried in vacuo to yield 7A.

B. 2-Chloroimidazo[1,5-a]pyrido[3,2-e]pyrazin-6(5H)-one

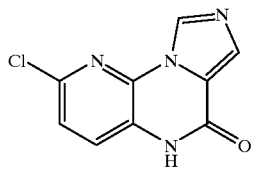

Compound 7B was prepared by an analogous method as that of 1B, except the reaction was at 130° C.

C. 2,6-Dichloroimidazo[1,5-a]pyrido[3,2-e]pyrazine

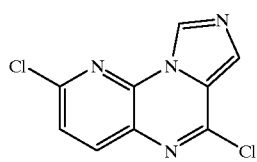

Compound 7C was prepared by an analogous method as that of 1C.

D. 2-Chloro-N-(2-chloro-6-methylphenyl)imidazo[1,5-a]pyrido[3,2-e]pyrazin-6-amine Compound 7D was prepared by an analogous method to that of 1D. HPLC ret. time: 4.066 min. (method of Example 1).

EXAMPLE 8

Preparation of N-(2-Chloro-6-methylphenyl)-2-(4-methyl-1-piperazinyl)imidazo[1,5-a]pyrido[3,2-e]pyrazin-6-amine

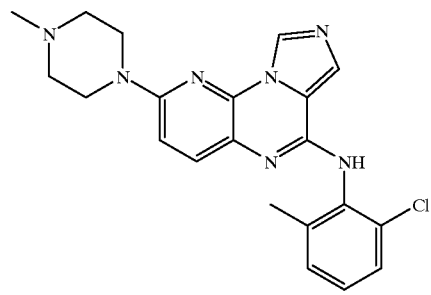

To 7D (300 mg, 0.87 mmol) was added N-methylpiperazine (5 mL). The mixture was heated to 180° C. for 2 h then cooled to room temperature. Water and saturated sodium bicarbonate was added to the reaction and the solid product was collected by filtration with several water washes. The product was dried in vacuo to yield 8. HPLC ret. time: 2.114 min. (method of Example 1).

EXAMPLES 9 TO 46

The following compounds 9 to 46 (Examples 9 to 46) were prepared by an analogous method to that of 8 (Example 8). These compounds have the structure shown below:

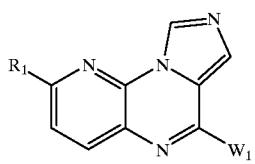

where $R_1$ and $W_1$ are defined in the following Table 2. The HPLC retention times of Table 2 were obtained by the method of Example 1. "$X_1$" and "$X_2$" in Table 2 are not substituents, but rather show the point of attachment of $R_1$ and $W_1$, respectively, to the remainder of the compound of formula I. Unfilled valences on nitrogen indicate the presence of a hydrogen.

TABLE 2

| Ex. No. | $R_1$ | $W_1$ | Compound Name | HPLC Ret. time (min.) |
|---|---|---|---|---|
| 9 | | | N-(2-Chloro-6-methylphenyl)-2-(4-morpholinyl)imidazo[1,5-a]pyrido[3,2-e]pyrazin-6-amine | 3.202 |
| 10 | | | $N^6$-(2-Chloro-6-methylphenyl)-$N^2$-[2-(4-morpholinyl)ethyl]imidazo[1,5-a]pyrido[3,2-e]pyrazine-2,6-diamine | 2.069 |
| 11 | | | N-(2-Chloro-6-methylphenyl)-2-[2-(4-morpholinyl)ethoxy]imidazo[1,5-a]pyrido[3,2-e]pyrazin-6-amine | 2.251 |
| 12 | | | $N^6$-(2-Chloro-6-methylphenyl)-$N^2$-(3-pyridinylmethyl)imidazo[1,5-a]pyrido[3,2-e]pyrazine-2,6-diamine | 2.231 |
| 13 | | | N-(2-Chloro-6-methylphenyl)-2-(2-methoxyethoxy)imidazo[1,5-a]pyrido[3,2-e]pyrazin-6-amine | 3.429 |
| 14 | | | N-(2-Chloro-6-methylphenyl)-2-(1-piperazinyl)imidazo[1,5-a]pyrido[3,2-e]pyrazin-6-amine | 2.167 |

TABLE 2-continued

| Ex. No. | R₁ | W₁ | Compound Name | HPLC Ret. time (min.) |
|---|---|---|---|---|
| 15 | 3,5-dimethylpiperazinyl (N-X₁) | 2-chloro-6-methylphenyl-NH (X₂) | N-(2-Chloro-6-methylphenyl)-2-(3,5-dimethyl-1-piperazinyl)imidazo[1,5-a]pyrido[3,2-e]pyrazin-6-amine | 2.325 |
| 16 | 4-(2-pyridinyl)piperazinyl | 2-chloro-6-methylphenyl-NH | N-(2-Chloro-6-methylphenyl)-2-[4-(2-pyridinyl)-1-piperazinyl]imidazo[1,5-a]pyrido[3,2-e]pyrazin-6-amine | 2.633 |
| 17 | 4-phenylpiperazinyl | 2-chloro-6-methylphenyl-NH | N-(2-Chloro-6-methylphenyl)-2-(4-phenyl-1-piperazinyl)imidazo[1,5-a]pyrido[3,2-e]pyrazin-6-amine | 3.945 |
| 18 | piperidinyl | 2-chloro-6-methylphenyl-NH | N-(2-Chloro-6-methylphenyl)-2-(1-piperidinyl)imidazo[1,5-a]pyrido[3,2-e]pyrazin-6-amine | 3.846 |
| 19 | 4,1'-bipiperidinyl | 2-chloro-6-methylphenyl-NH | 2-(4,1'-Bipiperidin-1-yl)-N-(2-chloro-6-methylphenyl)imidazo[1,5-a]pyrido[3,2-e]pyrazine-6-amine | 2.486 |
| 20 | 4-methylpiperidinyl | 2-chloro-6-methylphenyl-NH | N-(2-Chloro-6-methylphenyl)-2-(4-methyl-1-piperidinyl)imidazo[1,5-a]pyrido[3,2-e]pyrazin-6-amine | 4.117 |
| 21 | N-methyl-N-(1-methyl-4-piperidinyl)amino | 2-chloro-6-methylphenyl-NH | $N^6$-(2-Chloro-6-methylphenyl)-$N^2$-methyl-$N^2$-(1-methyl-4-piperidinyl)imidazo[1,5-a]pyrido[3,2-e]pyrazine-2,6-diamine | 2.397 |
| 22 | N-[2-(dimethylamino)ethyl]-N-ethylamino | 2-chloro-6-methylphenyl-NH | $N^6$-(2-Chloro-6-methylphenyl)-$N^2$-[2-(dimethylamino)ethyl]-$N^2$-ethylimidazo[1,5-a]pyrido[3,2-e]pyrazine-2,6-diamine | 2.478 |

TABLE 2-continued

| Ex. No. | R₁ | W₁ | Compound Name | HPLC Ret. time (min.) |
|---|---|---|---|---|
| 23 | imidazol-1-yl (N-X₁) | 2-chloro-6-methylphenyl-NH- (X₂) | N-(2-Chloro-6-methylphenyl)-2-(1H-imidazol-1-yl)imidazo[1,5-a]pyrido[3,2-e]pyrazin-6-amine | 2.667 |
| 24 | 4-ethyl-1-piperazinyl | 2-chloro-6-methylphenyl-NH- | N-(2-Chloro-6-methylphenyl)-2-(4-ethyl-1-piperazinyl)imidazo[1,5-a]pyrido[3,2-e]pyrazin-6-amine | 2.200 |
| 25 | 4-cyclohexyl-1-piperazinyl | 2-chloro-6-methylphenyl-NH- | N-(2-Chloro-6-methylphenyl)-2-(4-cyclohexyl-1-piperazinyl)imidazo[1,5-a]pyrido[3,2-e]pyrazin-6-amine | 2.680 |
| 26 | (CH₃)₂N-X₁ | 2-chloro-6-methylphenyl-NH- | $N^6$-(2-Chloro-6-methylphenyl)-$N^2$,$N^2$-dimethylimidazo[1,5-a]pyrido[3,2-e]pyrazine-2,6-diamine | 3.257 |
| 27 | (H₃CCH₂)₂N-X₁ | 2-chloro-6-methylphenyl-NH- | $N^6$-(2-Chloro-6-methylphenyl)-$N^2$,$N^2$-dimethylimidazo[1,5-a]pyrido[3,2-e]pyrazine-2,6-diamine | 3.701 |
| 28 | H₃C(CH₂)₃N(CH₃)-X₁ | 2-chloro-6-methylphenyl-NH- | $N^2$-Butyl-$N^6$-(2-chloro-6-methylphenyl)-$N^2$-methylimidazo[1,5-a]pyrido[3,2-e]pyrazine-2,6-diamine | 3.846 |
| 29 | Cl-X₁ | 2,6-dichlorophenyl-NH- | 2-Chloro-N-(2,6-dichlorophenyl)imidazo[1,5-a]pyrido[3,2-e]pyrazin-6-amine | 4.101 |
| 30 | 4-methyl-1-piperazinyl | 2,6-dichlorophenyl-NH- | N-(2,6-Dichlorophenyl)-2-(4-methyl-1-piperazinyl)imidazo[1,5-a]pyrido[3,2-e]pyrazin-6-amine | 2.297 |

TABLE 2-continued

| Ex. No. | R₁ | W₁ | Compound Name | HPLC Ret. time (min.) |
|---|---|---|---|---|
| 31 | 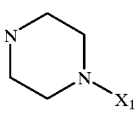 | 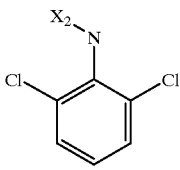 | N-(2,6-Dichlorophenyl)-2-(1-piperazinyl)imidazo[1,5-a]pyrido[3,2-e]pyrazin-6-amine | 2.363 |
| 32 | 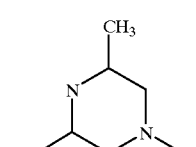 | 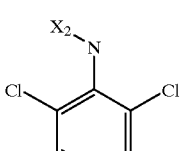 | N-(2,6-Dichlorophenyl)-2-(3,5-dimethyl-1-piperazinyl)imidazo[1,5-a]pyrido[3,2-e]pyrazin-6-amine | 2.536 |
| 33 | 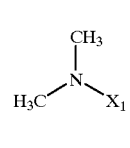 | 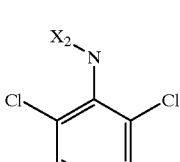 | $N^6$-(2,6-Dichlorophenyl)-$N^2,N^2$-dimethylimidazo[1,5-a]pyrido[3,2-e]pyrazine-2,6-diamine | 3.489 |
| 34 | 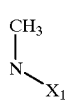 | 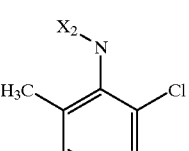 | $N^6$-(2-Chloro-6-methylphenyl)-$N^2$-methylimidazo[1,5-a]pyrido[3,2-e]pyrazine-2,6-diamine | 2.928 |
| 35 | 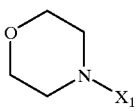 | 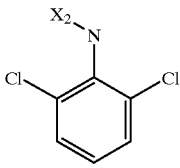 | N-(2,6-Dichlorophenyl)-2-(4-morpholinyl)imidazo[1,5-a]pyrido[3,2-e]pyrazin-6-amine | 3.440 |
| 36 | 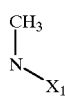 | 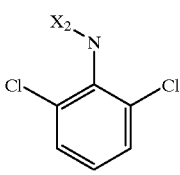 | $N^6$-(2,6-Dichlorophenyl)-$N^2$-methylimidazo[1,5-a]pyrido[3,2-e]pyrazine-2,6-diamine | 3.055 |
| 37 | 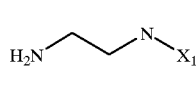 | 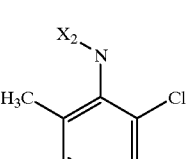 | $N^2$-(2-Aminoethyl)-$N^6$-(2-chloro-6-methylphenyl)imidazo[1,5-a]pyrido[3,2-e]pyrazine-2,6-diamine | 2.080 |
| 38 | 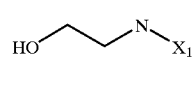 | 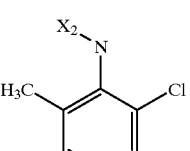 | $N^6$-(2-Chloro-6-methylphenyl)-$N^2$-(2-hydroxyethyl)imidazo[1,5-a]pyrido[3,2-e]pyrazine-2,6-diamine | 2.708 |

TABLE 2-continued

| Ex. No. | R₁ | W₁ | Compound Name | HPLC Ret. time (min.) |
|---|---|---|---|---|
| 39 | (2,2,2-trifluoroethyl-piperazinyl-X₁) | (2-chloro-6-methylphenyl-NX₂) | N-(2-Chloro-6-methylphenyl)-2-[4-(2,2,2-trifluoroethyl)-1-piperazinyl]imidazo[1,5-a]pyrido[3,2-e]pyrazin-6-amine | 3.196 |
| 40 | (2,2,2-trifluoroethyl-piperazinyl-X₁) | (2,6-dichlorophenyl-NX₂) | N-(2,6-Dichlorophenyl)-2-[4-(2,2,2-trifluoroethyl)-1-piperazinyl]imidazo[1,5-a]pyrido[3,2-e]pyrazin-6-amine | 3.989 |
| 41 | H₂N-CH₂CH₂-NH-X₁ | (2,6-dichlorophenyl-NX₂) | $N^2$-(2-Aminoethyl)-$N^6$-(2,6-dichlorophenyl)imidazo[1,5-a]pyrido[3,2-e]pyrazine-2,6-diamine | 2.264 |
| 42 | H₃C-(4-methylpiperazinyl-X₁) | (4-bromo-2-chloro-6-methylphenyl-NX₂) | N-(4-Bromo-2-chloro-6-methylphenyl)-2-(4-methyl-1-piperazinyl)imidazo[1,5-a]pyrido[3,2-e]pyrazin-6-amine | 3.039 |
| 43 | H₃C-(4-methylpiperazinyl-X₁) | (3,5-dichloro-4-amino-N-cyclopropyl benzamide-NX₂) | N-Cyclopropyl-3,5-dichloro-4-[[2-(4-methyl-1-piperazinyl)imidazo[1,5-a]pyrido[3,2-e]pyrazin-6-yl]amino]benzamide | 2.500 |
| 44 | H₃C-C(O)NH-pyrrolidinyl-X₁ | (2-chloro-6-methylphenyl-NX₂) | N-[1-[6-[(2-Chloro-6-methylphenyl)amino]imidazo[1,5-a]pyrido[3,2-e]pyrazin-2-yl]-3-pyrrolidinyl]acetamide | 3.022 |

TABLE 2-continued

| Ex. No. | R₁ | W₁ | Compound Name | HPLC Ret. time (min.) |
|---|---|---|---|---|
| 45 | | | N-[1-[6-[(2-Chloro-6-methlyphenyl)amino]imidazo[1,5-a]pyrido[3,2-e]pyrazin-2-yl]-3-pyrrolidinyl]-N-methylacetamide | 3.108 |
| 46 | | | 4-[6-[(2-Chloro-6-methylphenyl)amino]imidazo[1,5-a]pyrido[3,2-e]pyrazin-2-yl]piperazinone | 2.834 |

EXAMPLE 47

Preparation of 1-Acetyl-4-[6-[(2-chloro-6-methylphenyl)amino]imidazo[1,5-a]pyrido[3,2-e]pyrazin-2-yl]piperazine

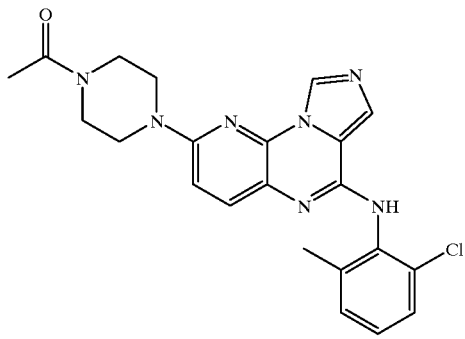

To 14 (20 mg, 0.05 mmol) in dichloromethane (0.4 mL) cooled in an ice-bath was added acetic anhydride (5.3 μL, 0.056 mmol). The reaction was warmed to room temperature for 0.5 h then water and saturated sodium bicarbonate was added and the dichloromethane removed in vacuo. The solid product was collected by filtration with water rinses then dried under high vacuum to yield 47. HPLC ret. time: 3.040 min. (method of Example 1).

EXAMPLES 48 TO 50

The following compounds 48 to 50 (Examples 48 to 50) were prepared from 14 by methods analogous to that used for the preparation of 47. These compounds have the structure shown below:

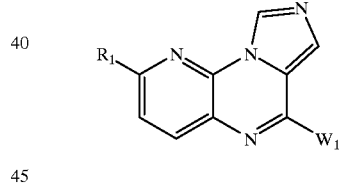

where R₁ and W₁ are defined in the following Table 3. The HPLC retention times of Table 3 were obtained by the method of Example 1. "X₁" and "X₂" in Table 3 are not substituents, but rather show the point of attachment of R₁ and W₁, respectively, to the remainder of the compound of formula I. Unfilled valences on nitrogen indicate the presence of a hydrogen.

TABLE 3

| Ex. No. | R₁ | W₁ | Compound Name | HPLC Ret. time (min) |
|---|---|---|---|---|
| 48 | (methylsulfonyl-piperazine structure) | (2-chloro-6-methylphenylamino structure) | 4-[6-[(2-Chloro-6-methylphenyl)amino]imidazo[1,5-a]pyrido[3,2-e]pyrazin-2-yl]-1-(methylsulfonyl)piperazine | 3.067 |
| 49 | (methyl carbamate piperazine structure) | (2-chloro-6-methylphenylamino structure) | 4-[6-[(2-Chloro-6-methylphenyl)amino]imidazo[1,5-a]pyrido[3,2-e]pyrazin-2-yl]-1-piperazinecarboxylic acid methyl ether | 3.440 |
| 50 | (acetylpiperazine structure) | (2,6-dichlorophenylamino structure) | 1-Acetyl-4-[6-[(2,6-dichlorophenyl)amino]imidazo[1,5-a]pyrido[3,2-e]pyrazin-2-yl]piperazine | 3.243 |

EXAMPLE 51

Preparation of N-(2-Chloro-6-methylphenyl)imidazo[1,5-a]pyrido[2,3-e]pyrazin-4-amine

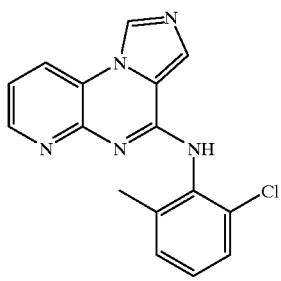

A. N-[(2,4-Dimethoxyphenyl)methyl]-3-nitro-2-pyridinamine

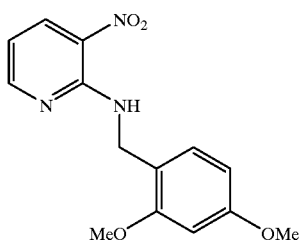

The mixture of 3-nitro-2-chloropyridine (159 mg, 1.0 mmol), 2,4-dimethoxybenzyl amine hydrogen chloride (244 mg, 1.2 mmol) and diisopropylethylamine (0.436 ml, 2.5 mmol) in 1.0 ml of dry DMF was heated at 125° C. for 1.0 h, then cooled to room temperature. The mixture was diluted with water, and extracted with ethylacetate (x2). The combined organic extracts were washed with water and brine, and dried over anhydrous Na₂SO₄. Concentration in vacuo gave crude 51A which was used directly in next step without further purification.

B. N²-[(2,4-Dimethoxyphenyl)methyl]-2,3-pyridinediamine

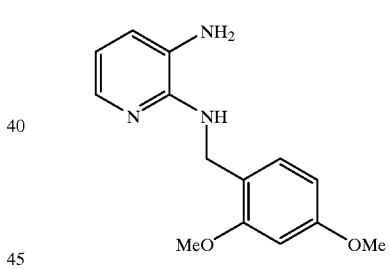

the mixture of crude 51A (661 mg) and 150 mg of 10% Pd-C in 10 ml of MeOH was stirred under hydrogen atmosphere for 4.0 h. The catalyst was removed by filtration and the filtrate was concentrated in vacuo to give 612 mg of crude 51B which was used directly in next step without further purification.

C. 4-[(2,4-Dimethoxyphenyl)methyl]pyrido[2,3-b]pyrazin-3(4H)-one

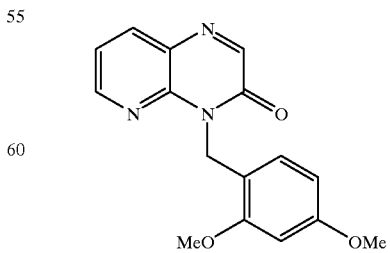

The mixture of crude 51B (612 mg) and ethyl glyoxylate (0.476 ml, 2.4 mmol, 50% solution in toluene) in 2.5 ml of ethanol was heated to reflux for 2.0 hrs. Upon cooling to room temperature, the mixture was let standing overnight. The crystalline material was collected by filtration and washed with cold ethanol, and dried under high vacuum to give 228.3 mg of 51C as a pale-yellow needle.

D. 5-[(2,4-Dimethoxyphenyl)methyl]imidazo[1,5-a]pyrido[2,3-e]pyrazin-4(5H)-one

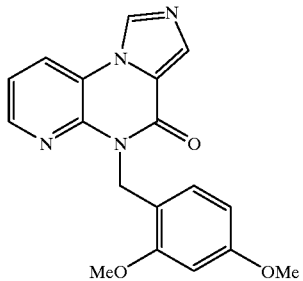

56 mg of NaH (60% dispersion in mineral oil, 1.39 mmol) was washed once with hexane and suspended in 1.5 ml of dry THF. To this suspension cooled at 0° C. was added a mixture of 51C (188 mg. 0.632 mmol) and tosylmethyl isocyanide (136 mg, 0.696 mmol) in dry THF (3.5 ml). The reaction mixture was stirred at 0° C. for 30 min, warmed to room temperature and stirred for an additional 1.0 hr. The reaction mixture was poured onto a mixture of ice-water (15 ml). The precipitate was collected by filtration and washed with water and ether. Drying under high vacuum gave 185 mg of 51D as an off-white solid.

E. Imidazo[1,5-a]pyrido[2,3-e]pyrazin-4(5H)-one

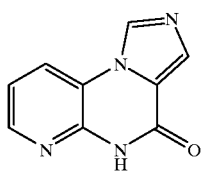

A solution of 185 mg of 51D in 3 ml of trifluoroacetic acid was stirred at room temperature for 3.0 hrs. The mixture was concentrated in vacuo, and the residue was taken in water (5 ml). To this was carefully added a solution of saturated NaHCO$_3$ until the pH was neutral. The precipitate was collected by filtration and washed with water and ether. Drying under high vacuum gave 121 mg of 51E as a light yellow solid.

F. 4-Chloroimidazo[1,5-a]pyrido[2,3-e]pyrazine

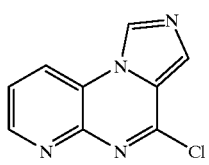

A mixture of 189 mg of 51E and 3 ml of phosphorus oxychloride was heated to reflux overnight. The mixture was concentrated in vacuo, and the residue was taken in ice-water (5 ml). To this was carefully added a solution of saturated NaHCO$_3$ until the pH was neutral. Ethyl acetate was used for extraction (X3), and the combined organic extracts were dried over anhydrous Na$_2$SO$_4$. Concentration in vacuo gave 39 mg of 51F as an orange solid.

G. N-(2-Chloro-6-methylphenyl)imidazo[1,5-a]pyrido[2,3-e]pyrazin-4-amine

The title compound 51G was prepared from 51F by a route analogous to that used for the preparation of 1D. HPLC ret. time: 2.389 min. (YMC ODS-A C18 S-5column, 4.6×50 mm. 4 min gradient from 0 to 100% B with 2 min hold at 100% B. Solvent A: 90%H$_2$)—10%MeOH—0.2%H$_3$PO$_4$; Solvent B: 10%H$_2$O—90%MeOH—0.2%H$_3$PO$_4$).

EXAMPLE 52

Preparation of N-(2,6-Dimethylphenyl)imidazol[1,5-a]pyrido[2,3-e]pyrazin-4-amine

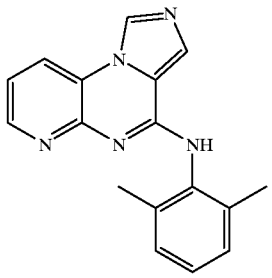

The title compound 52 was prepared from 51F by a route analogous to that used for the preparation of 1D. HPLC ret. time: 2.292 min. (method of Example 51).

EXAMPLE 53

Preparation of N-(2,6-Dimethylphenyl)imidazo[1,5-a]pyrido[3,4-e]pyrazin-4-amine

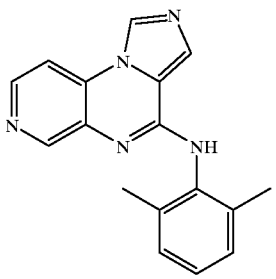

A. 4-[(4-Methoxyphenyl)methyl]pyrido[3,4-b]pyrazin-3(4H)-one

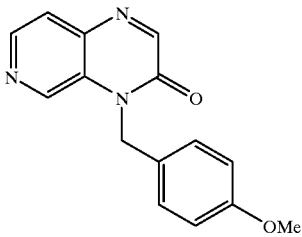

Compound 53A was prepared from 3,4-diaminopyridine by a route analogous to that used for the preparation of 51C.

B. 5-[(4-Methoxyphenyl)methyl]imidazo[1,5a]pyrido[3,4-e]pyrazin-4(5H)-one

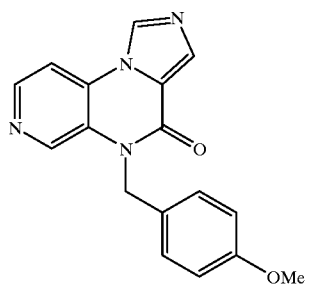

Compound 53B was prepared by a method analogous to that used for the preparation of 51D.

C. Imidazo[1,5-a]pyrido[3,4-e]pyrazin-4(5H)-one

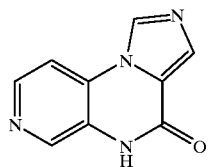

Compound 53C was prepared by a method analogous to that used for the preparation of 51E.

D. 4-Chloroimidazo[1,5-a]pyrido[3,4-e]pyrazine

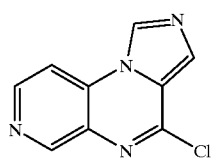

Compound 53D was prepared by a method analogous to that used for the preparation of 51F.

E. N(2,6-Dimethylphenyl)imidazo[1,5-a]pyrido[3,4-]pyrazin-4-amine

The title compound 53E was prepared from 53D by a method analogous to that used for the preparation of 1D. HPLC Retention time: 4.75 min. (YMC ODS-A C18 S-3 column, 6×150 mm; 25 min linear gradient from 40%–100% B with 5 min hold at 100% B (A=90% H$_2$O/MeOH+0.2% H$_3$PO$_4$; B=90% MeOH/H$_2$O+0.2% H$_3$PO$_4$).

EXAMPLE 54

Preparation of N-(2-Chloro-6-methylphenyl)imidazo[1,5-a]pyrido[3,4-e]pyrazin-4-amine

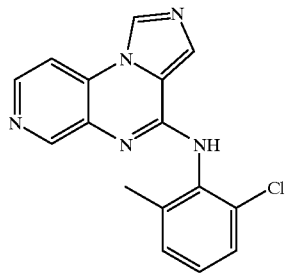

The title compound 54 was prepared from 53D by a method analogous to that used for the preparation of 1D. HPLC Retention time: 2.47 min. (YMC ODS-A C18 S-3column, 6×150 mm; 25 min linear gradient from 50%–100% B with 5 min hold at 100% B (A=90% H$_2$O/MeOH+0.2% H$_3$PO$_4$; B=90% MeOH/H$_2$O+0.2% H$_3$PO$_4$).

EXAMPLE 55

Preparation of N-(2-Chloro-6-methylphenyl)-2-(hexahydro-1H-1,4-diazepin-1-yl)imidazo[1,5-a]pyrido[3,2-e]pyrazin-6-amine

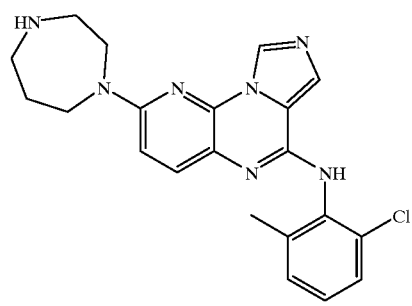

The title compound 55 was prepared from 7D by a method analogous to that used for the preparation of 8. HPLC Retention time: 2.250 min. (method of Example 1).

EXAMPLE 56

Preparation of N-(2-Chloro-6-methylphenyl)-2-(hexahydro-4-methyl-1H-1,4-diazepin-1-yl)imidazo[1,5-a]pyrido[3,2-e]pyrazin-6-amine

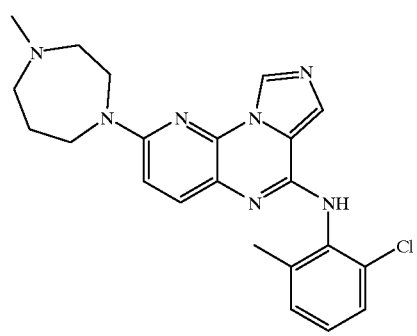

The title compound 56 was prepared from 7D by a method analogous to that used for the preparation of 8. HPLC Retention time: 2.196 min. (method of Example 1).

EXAMPLE 57

Preparation of N-(2-Chloro-6-methylphenyl)-2-phenylimidazo[1,5-a]pyrido[3,2-e]pyrazin-6-amine

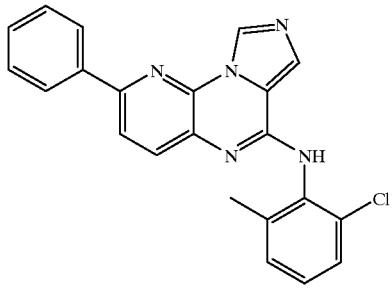

A mixture of 7D (51 mg; 0.15 mmol), benzeneboronic acid (40 mg; 0.3 mmol), 0.7 mL of 2 M sodium carbonate solution, 0.8 mL of EtOH and 1 mL of dry toluene was heated to 85° C. with rapid stirring for 2 hr. After cooling, the reaction mixture was partitioned between EtOAc and water. The organic layer was washed with brine, dried ($MgSO_4$) and concentrated. The residue was filtered through silica gel using a mixture of EtOAc-hexane as the eluent. Concentration in vacuo afforded, after trituration with MeOH, 30 mg (52%) of the title compound 57 as a light yellow solid. HPLC Retention time: 22.67 min. (YMC ODS-A C18 S-3column, 6×150 mm; 25 min linear gradient from 40%–100% B with 5 min hold at 100% B (A=90% $H_2O$/MeOH+0.2% $H_3PO_4$; B=90%MeOH/$H_2O$+0.2% $H_3PO_4$).

EXAMPLE 58

Preparation of N-(2-Chloro-6-methylphenyl)-2-(4-methoxyphenyl)imidazo[1,5-a]pyrido[3,2-e]pyrazin-6-amine

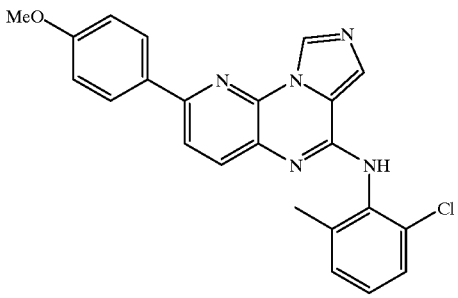

The title compound 58 was prepared from 7D by a method analogous to that used for the preparation of 57. HPLC Retention time: 5.72 min. (YMC ODS-A C18 S-3 column, 6×150 mm; 25 min linear gradient from 50%–100% B with 5 min hold at 100% B (A=90% $H_2O$/MeOH+0.2% $H_3PO_4$; B=90%MeOH/$H_2O$+0.2% $H_3PO_4$).

EXAMPLE 59

Preparation of N-(2-Chloro-6-methylphenyl)-3-methoxyimidazo[1,5-f]pteridin-6-amine

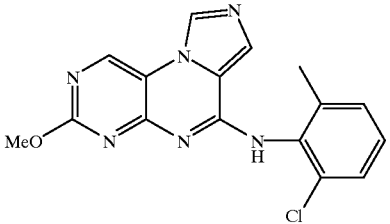

A. N-(2-Chloro-5-fluoro-4-pyrimidinyl)-1H-imidazole-2-carboxamide

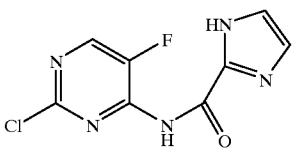

Compound 59A was prepared from 4-amino-2-chloro-5-fluoropyrimidine by a route analogous to that used for the preparation of 1A.

B. 3-Chloroimidazo[1,5-f]pteridin-6(5H)-one

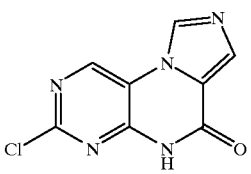

Compound 59B was prepared from 59A by a method analogous to that used for the preparation of 1B.

C. 3-Methoxyimidazo[1,5-f]pteridin-6(5H)-one

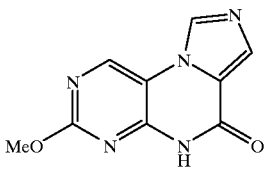

A solution of 59B (500 mg, 2.25 mmol) in 9 mL of dry DMF was added to a solution of sodium methoxide (257 mg. 4.51 mmol) in 4.5 mL of DMF. The mixture was heated to reflux for 8 hours, then filtered through celite, washed with dry DMF. The filtrate was concentrated in vacuo followed by addition of sat. $NH_4Cl$ and water. The solid was collected by filtration and triturated with ethanol at 70° C. for 3 hours, and finally collected by filtration and dried in vacuo to give compound 59C.

D. 6-Chloro-3-methoxyimidazo[1,5-f]pteridine

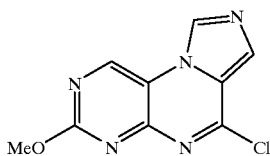

Compound 59D was prepared from 59C by a method analogous to that used for the preparation of 1C.

E. N-(2-Chloro-6-methylphenyl)-3-methoxyimidazo[1,5-f]pteridin-6-amine

The title compound 59E was prepared from 59D by a method analogous to that used for the preparation of 1D. HPLC Retention time: 3.53 min. (method of Example 51).

EXAMPLE 60

Preparation of N-(2-Chloro-6-methylphenyl)-1,8-dimethyldiimidazo[1,5-a:4',5'-e]pyrazin-5-amine

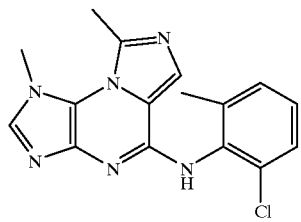

A. 2-Chloro-1-methyl-3-nitro-1H-imidazole

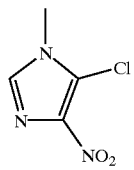

5-Chloro-1-methyl-imidazole (4.0 g, 34.32 mmol) was dissolved in a mixture of 4.0 g of conc. nitric acid and 14 mL of water, and concentrated in vacuo to give a yellow slurry. To this mixture was added dropwise 12 g of conc. sulfuric acid and heated to 95° C. for 2 hours. Upon cooling, ice was added to the reaction mixture, which was then left standing 10 hours at 5° C. The white precipitation was collected by filtration, washed with water, recrystallized from ethanol and dried in vacuo to give compound 60A.

B. 1,2'-Dimethyl[5,1'-bi1H-imidazol]-4-amine

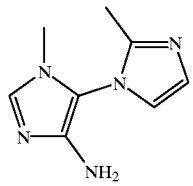

60A (427 mg. 2.06 mmol) in 12 mL of methanol containing 200 mg of Pd/C was stirred under hydrogen atmosphere for 3 hours. The mixture was filtered through celite, washed with methanol, and the filtrate concentrated in vacuo to give compound 60B.

N-(2-Chloro-6-methylphenyl)-N'-(1,2'-dimethyl[5,1'-bi-1H-imidazol]-4-yl)urea

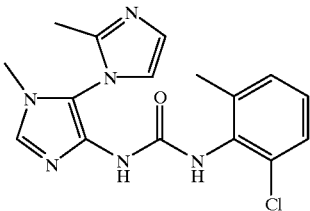

2-Chloro-6-methylphenyl isocynate (86 μL, 0.62 mmol) was added to a solution of 60B (100 mg. 0.56 mmol) in 2.8 mL of DMF at 0° C. The mixture was stirred at room temperature for 20 min. Water was added, the mixture was extracted with ethyl acetate, and the organic layer was washed with brine, dried over sodium sulfate, and concentrated in vacuo. The resulting solid was triturated with ether to give compound 60C.

D. N-(2-Chloro-6-methylphenyl)-1,8-dimethyldiimidazo[1,5-a:4',5'-e]pyrazin-5-amine To 60C (40 mg, 0.12 mmol) was added 12 mL of dry pyridine, phosphorous oxychloride (16 μL, 0.17 mmol) and 4-dimethylaminopyridine (21 mg, 0.17 mmol). the mixture was heated to reflux for 10 hours. The reaction mixture was concentrated in vacuo and cooled to 0° C. Water was added to the residue and the mixture was neutralized with saturated sodium bicarbonate, and extracted with ethyl acetate. The organic layer was dried over sodium sulfate and concentrated in vacuo to give the title compound 60D. HPLC Rentention time: 2.04 min. (method of Example 51).

EXAMPLE 61

Preparation of N-(2-Chloro-6-methylphenyl)-1,3,8-trimethylimidazo[1,5-a]pyrazolo[4,3-e]pyrazin-5-amine

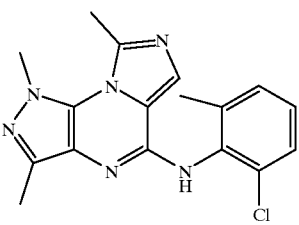

The title compound 61 was prepared starting from 5-chloro-1,3-dimethyl-4-nitropyrazole by a route analogous to that used for the preparation of 60D. HPLC Retention time: 2.04 min. (method of Example 51).

EXAMPLE 62

Preparation of N-(2-Fluoro-6-methylphenyl)-2-(1-piperazinyl)imidazol[1,5-a]pyrido[3,2-e]pyrazin-6-amine

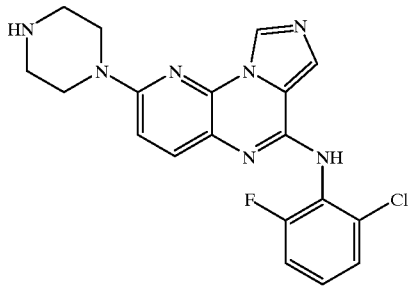

The title compound 62 was prepared from 7C by a route analogous to that used for the preparation of 8. HPLC Retention time: 2.243 min. (method of Example 1).

EXAMPLE 63

Preparation of 2-(3,5-Dimethyl-1-piperazinyl)-N-(2-fluoro-6-methylphenyl)imidazo[1,5-a]pyrido[3,2-e]pyrazin-6-amine

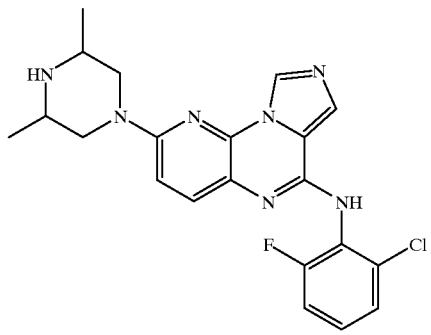

The title compound 63 was prepared from 7C by a route analogous to that used for the preparation of 8. HPLC Retention time: 2.396 min. (method of Example 1).

EXAMPLES 64–168

Following compounds 64–168 were prepared from 7C by an analogous method as that of 8. These compounds have the structure shown below:

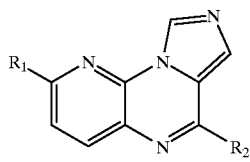

where $R_1$ and $R_2$ are defined in the following Table 4. The HPLC retention times of Table 4 were obtained by the method of Example 1. "$X_1$" and "$X_2$" in Table 4 are not substitutents, but rather show the point of attachment of $R_1$ and $R_2$, respectively, to the remainder of the compound of formula I. Unfilled valences on nitrogen indicate the presence of a hydrogen.

TABLE 4

| Ex. No | $R_1$ | $R_2$ | Compound name | HPLC time (min) |
|---|---|---|---|---|
| 64 | H₃C–N(piperazine)–X₁ | X₂–NH–(2-F,6-Cl-phenyl) | N-(2-Chloro-6-fluorophenyl)-2-(4-methyl-1-piperazinyl)imidazo[1,5-a]pyrido[3,2-e]pyrazin-6-amine | 2.226 |
| 65 | CH₃CH₂–N(piperazine)–X₁ | X₂–NH–(2-F,6-Cl-phenyl) | N-(2-Chloro-6-fluorophenyl)-2(4-ethyl-1-piperazinyl)imidazo[1,5-a]pyrido[3,2-e]pyrazin-6-amine | 2.274 |

TABLE 4-continued

| Ex. No | R₁ | R₂ | Compound name | HPLC time (min) |
|---|---|---|---|---|
| 66 | 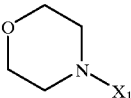 | 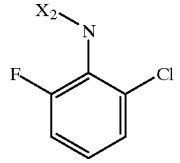 | N-(2-Chloro-6-fluorophenyl)-2-(4-morpholinyl)imidazo[1,5-a]pyrido[3,2-e]pyrazin-6-amine | 3.339 |
| 67 | 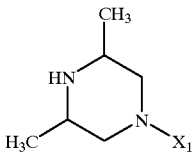 | 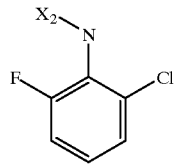 | N-(2-Chloro-6-fluorophenyl)-2-(2,6-dimethyl-4-morpholinyl)imidazo[1,5-a]pyrdio[3,2-e]pyrazin-6-amine | 3.849 |
| 68 | 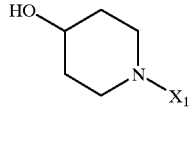 | 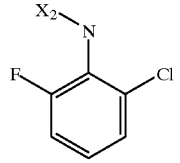 | 1-[6-[(2-Chloro-6-fluorophenyl)amino]imidazo[1,5-a]pyrido[3,2-e]pyrazin-2-yl]-4-piperidinol | 3.176 |
| 69 | 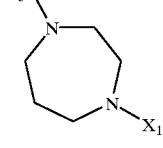 | 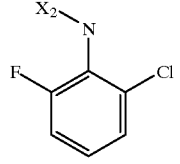 | N-(2-Chloro-6-fluorophenyl)-2-(hexahydro-4-methyl-1H-1,4-diazepin-1-yl)imidazo[1,5-a]pyrido[3,2-e]pyrazin-6-amine | 2.338 |
| 70 | 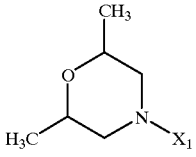 | 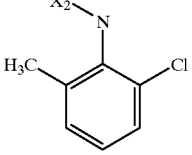 | N-(2-Chloro-6-methylphenyl)-2-(2,6-dimethyl-4-morpholinyl)imidazo[1,5-a]pyrido[3,2-e]pyrazin-6-amine | 3.635 |
| 71 | 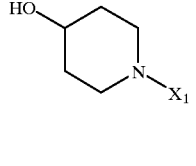 | 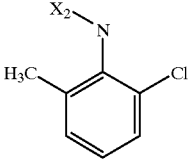 | 1-[6-[(2-Chloro-6-methylphenyl)amino]imidazo[1,5-a]pyrido[3,2-e]pyrazin-2-yl]-4-piperidinol | 3.036 |
| 72 |  | 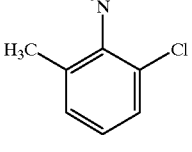 | N-(2-Chloro-6-methylphenyl)-2-methoxyimidazo[1,5-a]pyrido[3,2-e]pyrazin-6-amine | 3.495 |
| 73 | 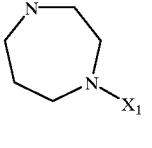 | 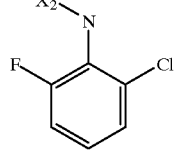 | N-(2-Chloro-6-methylphenyl)-2-(hexahydro-1H-1,4-diazepin-1-yl)imidazo[1,5-a]pyrido[3,2-e]pyrazin-6-amine | 2.309 |

TABLE 4-continued

| Ex. No | R₁ | R₂ | Compound name | HPLC time (min) |
|---|---|---|---|---|
| 74 | HO-CH₂CH₂-N(piperazine)-X₁ | X₂-NH-(2-F,6-Cl phenyl) | 4-[6-[(2-Chloro-6-fluorophenyl)amino]imidazo[1,5-a]pyrido[3,2-e]pyrazin-1-yl]-2-piperazineethanol | 2.200 |
| 75 | morpholinyl-CH₂CH₂-N(piperazine)-X₁ | X₂-NH-(2-F,6-Cl phenyl) | N-(2-Chloro-6-fluoropehnyl)-2-[4-[2-(4-morpholinyl)ethyl]-1-piperazinyl]imidazo[1,5-a]pyrido[3,2-e]pyrazin-6-amine | 2.000 |
| 76 | (H₃C)₂N-CH₂CH₂CH₂-N(piperazine)-X₁ | X₂-NH-(2-F,6-Cl phenyl) | N-(2-Chloro-6-fluorophenyl)-2-[4-[3-(dimethylamino)propyl]-1-piperazinyl]imidazo[1,5-a]pyrido[3,2-e]pyrazin-6-amine | 1.870 |
| 77 | CH₃O-CH₂CH₂-N(piperazine)-X₁ | X₂-NH-(2-F,6-Cl phenyl) | N-(2-Chloro-6-fluoropehnyl)-2-[4-(2-methoxyethyl)-1-piperazinyl]imidazo[1,5-a]pyrido[3,2-e]pyrazin-6-amine | 2.319 |
| 78 | (H₃C)₂N-CH₂CH₂-N(piperazine)-X₁ | X₂-NH-(2-F,6-Cl phenyl) | N-(2-Chloro-6-fluorophenyl)-2-[4-[2-(dimethylamino)ethyl]-1-piperazinyl]imidazo[1,5-a]pyrido[3,2-e]pyrazin-6-amine | 1.954 |
| 79 | CH₃O-CH₂CH₂-N(piperazine)-X₁ | X₂-NH-(2-CH₃,6-Cl phenyl) | N-(2-Chloro-6-methylphenyl)-2-[4-(2-methoxyethyl)-1-piperazinyl]imidazo[1,5-a]pyrido[3,2-e]pyrazin-6-amine | 2.197 |
| 80 | (H₃C)₂N-CH₂CH₂-N(piperazine)-X₁ | X₂-NH-(2-CH₃,6-Cl phenyl) | N-(2-Chloro-6-methylphenyl)-2-[4-[2-(dimethylamino)ethyl]-1-piperazinyl]imidazo[1,5-a]pyrido[3,2-e]pyrazin-6-amine | 1.863 |

TABLE 4-continued

| Ex. No | R₁ | R₂ | Compound name | HPLC time (min) |
|---|---|---|---|---|
| 81 | 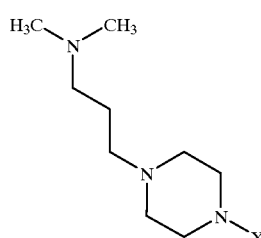 | 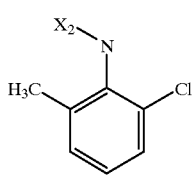 | N-(2-Chloro-6-methylphenyl)-2-[4-[3-dimethylamino)propyl]-1-piperazinyl]imidazo[1,5-a]pyrido[3,2-e]pyrazine-6-amine | 1.743 |
| 82 | 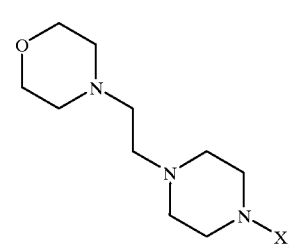 | 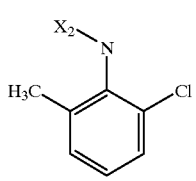 | N-(Chloro-6-methylphenyl)-2-[4-[2-(4-morpholinyl)ethyl]-1-piperazinyl]imidazo[1,5-a]pyrido[3,2-e]pyrazin-6-amine | 1.879 |
| 83 | 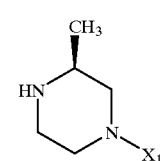 | 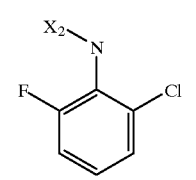 | (S)-N-(2-Chloro-6-fluorophenyl)-2-(3-methyl-1-piperazinyl)imidazol[1,5-a]pyrido[3,2-e]pyrazin-6-amine | 2.311 |
| 84 | 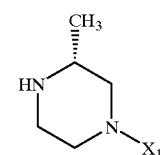 | 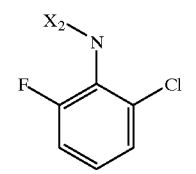 | (R)-N-(2-Chloro-6-fluorophenyl)-2-(3-methyl-1-piperazinyl)imidazo[1,5-a]pyrido[3,2-e]pyrazin-6-amine | 2.325 |
| 85 | 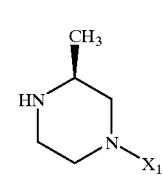 | 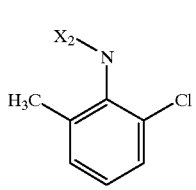 | (S)-N-(2-Chloro-6-methylphenyl)-2-(3-methyl-1-piperazinyl)imidazo[1,5-a]pyrido[3,2-e]pyrazin-6-amine | 2.181 |
| 86 | 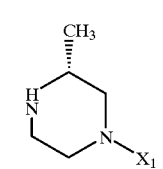 | 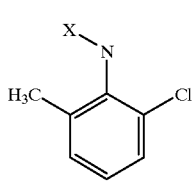 | (R)-N-(2-Chloro-6-methylphenyl)-2-(3-methyl-1-piperazinyl)imidazo[1,5-a]pyrido[3,2-e]pyrazin-6-amine | 2.192 |
| 87 | 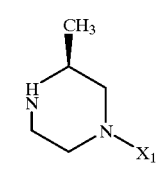 | 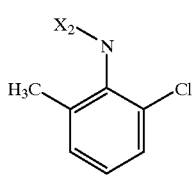 | (S)-N-(2,6-Dimethylphenyl)-2-(3-methyl-1-piperazinyl)imidazo[1,5-a]pyrido[3,2-e]pyrazin-6-amine | 1.974 |

TABLE 4-continued

| Ex. No | R₁ | R₂ | Compound name | HPLC time (min) |
|---|---|---|---|---|
| 88 | (R)-3-methylpiperazine | 2-chloro-6-methylaniline | (R)-N-(2,6-Dimethylphenyl)-2-(3-methyl-1-piperazinyl)imidazo[1,5-a]pyrido[3,2-e]pyrazin-6-amine | 1.987 |
| 89 | 3,5-dimethylpiperazine | 2,6-dimethylaniline | N-(2,6-Dimethylphenyl)-2-(3,5-dimethyl-1-piperazinyl)imidazo[1,5-a]pyrido[3,2-e]pyrazin-6-amine | 2.025 |
| 90 | piperazine | 2,6-dimethylaniline | N-(2,6-Dimethylphenyl)-2-(1-piperazinyl)imidazo[1,5-a]pyrido[3,2-e]pyrazin-6-amine | 1.906 |
| 91 | 4-[2-(dimethylamino)ethyl]piperazine | 2,6-dimethylaniline | 2-[4-[2-(Dimethylamino)ethyl]-1-piperazinyl]-N-(2,6-dimethylphenyl)imidazo[1,5-a]pyrido[3,2-e]pyrazin-6-amine | 1.658 |
| 92 | 4-methylpiperazine | 2,6-dimethylaniline | N-(2,6-Dimethylphenyl)-2-(4-methyl-1-piperazinyl)imidazo[1,5-a]pyrido[3,2-e]pyrazin-6-amine | 1.853 |
| 93 | hexahydro-1H-1,4-diazepine | 2,6-dimethylaniline | N-(2,6-Dimethylphenyl)-2-(hexahydro-1H-1,4-diazepin-1-yl)imidazo[1,5-a]pyrido[3,2-e]pyrazin-6-amine | 2.044 |
| 94 | hexahydro-4-methyl-1H-1,4-diazepine | 2,6-dimethylaniline | N-(2,6-Dimethylphenyl)-2-(hexahydro-4-methyl-1H-1,4-diazepin-1-yl)imidazo[1,5-a]pyrido[3,2-e]pyrazin-6-amine | 1.992 |
| 95 | (R)-3-hydroxypyrrolidine | 2,6-dimethylaniline | (R)-1-[6-[(2,6-Dimethylphenyl)amino]imidazol[1,5-a]pyrido[3,2-e]pyrazin-2-yl]-3-pyrrolidinol | 2.761 |

TABLE 4-continued

| Ex. No | R₁ | R₂ | Compound name | HPLC time (min) |
|---|---|---|---|---|
| 96 | (S)-3-hydroxypyrrolidin-1-yl connected via X₁ | 2,6-dimethylphenylamino connected via X₂ | (S)-1-[6-[(2,6-Dimethylphenyl)amino]imidazo[1,5-a]pyrido[3,2-e]pyrazin-2-yl]-3-pyrrolidinol | 2.772 |
| 97 | (R)-3-hydroxypyrrolidin-1-yl connected via X₁ | 2-chloro-6-methylphenylamino connected via X₂ | (R)-1-[6-[(2-Chloro-6-methylphenyl)amino]imidazo[1,5-a]pyrido[3,2-e]pyrazin-2-yl]-3-pyrrolidinol | 2.910 |
| 98 | (R)-3-(tert-butoxycarbonylamino)pyrrolidin-1-yl connected via X₁ | 2-chloro-6-methylphenylamino connected via X₂ | (R)-[1-[6-[(2-Chloro-6-methylphenyl)amino]imidazo[1,5-a]pyrido[3,2-e]pyrazin-2-yl]-3-pyrrolidinyl]carbamic acid 1,1-dimethylethyl ester | 3.648 |
| 99 | (S)-3-(tert-butoxycarbonylamino)pyrrolidin-1-yl connected via X₁ | 2-chloro-6-methylphenylamino connected via X₂ | (S)-[1-[6-[(2-Chloro-6-methylphenyl)amino]imidazo[1,5-a]pyrido[3,2-e]pyrazin-2-yl]-3-pyrrolidinyl]carbamic acid 1,1-dimethylethyl ester | 3.650 |
| 100 | pyrrolidin-1-yl connected via X₁ | 2-chloro-6-methylphenylamino connected via X₂ | N-(2-Chloro-6-methylpheynl)-2-(1-pyrrolidinyl)imidazo[1,5-a]pyrido[3,2-e]pyrazin-6-amine | 3.524 |
| 101 | 3-hydroxypyrrolidin-1-yl connected via X₁ | 2-chloro-6-methylphenylamino connected via X₂ | 1-[6-[(2-Chloro-6 methylphenyl)amino]imidazo[1,5-a]pyrido[3,2-e]pyrazin-2-yl]-3-pyrrolidinol | 2.921 |
| 102 | (R)-3-aminopyrrolidin-1-yl connected via X₁ | 2-chloro-6-methylphenylamino connected via X₂ | (R)-2-(3-Amino-1-pyrrolidinyl)-N-(2-chloro-6-methylphenyl)imidazo[1,5-a]pyrido[3,2-e]pyrazin-6-amine | 2.119 |

TABLE 4-continued

| Ex. No | R₁ | R₂ | Compound name | HPLC time (min) |
|---|---|---|---|---|
| 103 | (3-amino-pyrrolidinyl with X₁) | (2-chloro-6-methylphenylamino with X₂) | (S)-2-(3-Amino-1-pyrrolidinyl)-N-(2-chloro-6-methylphenyl)imidazo[1,5-a]pyrido[3,2-e]pyrazin-6-amine | 2.161 |
| 104 | (S)-2-(methoxymethyl)pyrrolidinyl with X₁ | (2-chloro-6-methylphenylamino with X₂) | (S)-N-(2-Chloro-6-methylphenyl)-2-[2-(methoxymethyl)-1-pyrrolidinyl]imidazo[1,5-a]pyrido[3,2-e]pyrazin-6-amine | 3.544 |
| 105 | (R)-2-(methoxymethyl)pyrrolidinyl with X₁ | (2-chloro-6-methylphenylamino with X₂) | (R)-N-(2-Chloro-6-methylphenyl)-2-[2-(methoxymethyl)-1-pyrrolidinyl]imidazo[1,5-a]pyrido[3,2-e]pyrazin-6-amine | 3.536 |
| 106 | 3-hydroxypiperidinyl with X₁ | (2-chloro-6-methylphenylamino with X₂) | 1-[6-[2-Chloro-6-methylphenyl)amino]imidazo[1,5-a]pyrido[3,2-e]pyrazin-2-yl]-3-piperidinol | 3.061 |
| 107 | 1,4-dioxa-8-azaspiro[4.5]decan-8-yl with X₁ | (2-chloro-6-methylphenylamino with X₂) | N-(2-Chloro-6-methylphenyl)-2-(1,4-dioxa-8-azaspiro[4.5]decan-8-yl)imidazo[1,5-a]pyrido[3,2-e]pyrazin-6-amine | 3.360 |
| 108 | (S)-3-(dimethylamino)pyrrolidinyl with X₁ | (2-chloro-6-methylphenylamino with X₂) | (S)-N-(2-Chloro-6-methylphenyl)-2-[3-(dimethylamino)-1-pyrrolidinyl]imidazo[1,5-a]pyrido[3,2-e]pyrazin-6-amine | 2.073 |
| 109 | 4-carboxamidopiperidinyl with X₁ | (2-chloro-6-methylphenylamino with X₂) | 1-[6-[(2-Chloro-6-methylphenyl)amino]imidazo[1,5-a]pyrido[3,2-e]pyrazin-2-yl]-4-piperidinecarboxamide | 2.802 |
| 110 | (R)-2-(hydroxymethyl)pyrrolidinyl with X₁ | (2-chloro-6-methylphenylamino with X₂) | (R)-1-[6-[(2-Chloro-6-methylphenyl)amino]imidazo[1,5-a]pyrido[3,2-e]pyrazin-2-yl]-2-pyrrolidinemethanol | 3.166 |

TABLE 4-continued

| Ex. No | R₁ | R₂ | Compound name | HPLC time (min) |
|---|---|---|---|---|
| 111 | (S)-2-(hydroxymethyl)pyrrolidine, N-X₁ | 2-chloro-6-methylphenyl-NH-X₂ | (S)-1-[6-[(2-Chloro-6-methylphenyl)amino]imidazo[1,5-a]pyrido[3,2-e]pyrazin-2-yl]-2-pyrrolidinemethanol | 3.194 |
| 112 | 2-(hydroxymethyl)piperidine, N-X₁ | 2-chloro-6-methylphenyl-NH-X₂ | 1-[6-[(2-Chloro-6-methylphenyl)amino]imidazo[1,5-a]pyrido[3,2-e]pyrazin-2-yl]-2-piperidinemethanol | 3.310 |
| 113 | 3-(hydroxymethyl)piperidine, N-X₁ | 2-chloro-6-methylphenyl-NH-X₂ | 1-[6-[(2-Chloro-6-methylphenyl)amino]imidazo[1,5-a]pyrido[3,2-e]pyrazin-2-yl]-3-piperidinemethanol | 3.234 |
| 114 | 4-(hydroxymethyl)piperidine, N-X₁ | 2-chloro-6-methylphenyl-NH-X₂ | 1-[6-[(2-Chloro-6-methyphenyl)amino]imidazo[1,5-a]pyrido[3,2-e]pyrazin-2-yl]-4-piperidinemethanol | 3.136 |
| 115 | 3-carboxamidopiperidine, N-X₁ | 2-chloro-6-methylphenyl-NH-X₂ | 1-[6-[(2-Chloro-6-methylphenyl)amino]imidazo[1,5-a]pyrido[3,2-e]pyrazin-2-yl]-3-piperidinecarboxamide | 2.921 |
| 116 | (S)-2-carboxamidopyrrolidine, N-X₁ | 2-chloro-6-methylphenyl-NH-X₂ | (S)-1-[6-[(2-Chloro-6-methylphenyl)amino]imidazo[1,5-a]pyrido[3,2-e]pyrazin-2-yl]-2-pyrrolidinecarboxamide | 3.721 |
| 117 | (R)-3-hydroxypyrrolidine, N-X₁ | 2-chloro-6-methylphenyl-NH-X₂ | (R)-1-[6-[(2-Chloro-6-methylphenyl)amino]imidazo[1,5-a]pyrido[3,2-e]pyrazin-2-yl]-3-pyrrolidinol | 2.721 |
| 118 | (R)-1-benzyl-3-aminopyrrolidine, NH-X₁ | 2-chloro-6-methylphenyl-NH-X₂ | (R)-N⁶-(2-Chloro-6-methylphenyl)-N²-[1-(phenylmethyl)-3-pyrrolidinyl]imidazo[1,5-a]pyrido[3,2-e]pyrazine-2,6-diamine | 2.923 |

TABLE 4-continued

| Ex. No | R₁ | R₂ | Compound name | HPLC time (min) |
|---|---|---|---|---|
| 119 | 1-benzyl-pyrrolidin-3-yl-NH-X₁ | 2-chloro-6-methylphenyl-NH-X₂ | (S)-N⁶-(2-Chloro-6-methylphenyl)-N²-[1-(phenylmethyl)-3-pyrrolidinyl]imidazo[1,5-a]pyrido[3,2-e]pyrazine-2,6-diamine | 2.696 |
| 120 | 4-methyl-1H-imidazol-1-yl-X₁ | 2-chloro-6-methylphenyl-NH-X₂ | N-(2-Chloro-6-methylphenyl)-2-(4-methyl-1H-imidazol-1-yl)imidazo[1.5-a]pyrido[3,2-e]pyrazin-6-amine | 2.737 |
| 121 | (R)-pyrrolidin-3-yl-NH-X₁ | 2-chloro-6-methylphenyl-NH-X₂ | (R)-N⁶-(2-Chloro-6-methylphenyl)-N²-(3-pyrrolidinyl)imidazo[1,5-a]pyrido[3,2-e]pyrazine-2,6-diamine | 2.170 |
| 122 | (S)-pyrrolidin-3-yl-NH-X₁ | 2-chloro-6-methylphenyl-NH-X₂ | (S)-N⁶-(2-Chloro-6-methylphenyl)-N²-(3-pyrrolidinyl)imidazo[1,5-a]pyrido[3,2-e]pyrazine-2,6-diamine | 2.171 |
| 123 | HOCH₂CH₂-N(CH₃)-X₁ | 2-chloro-6-methylphenyl-NH-X₂ | 2-[[6-(2-Chloro-6-methylphenyl)amino]imidazo[1,5-a]pyrido[3,2-e]pyrazin-2-yl]methylamino]ethanol | 2.894 |
| 124 | (HOCH₂CH₂)₂N-X₁ | 2-chloro-6-methylphenyl-NH-X₂ | 2,2'-[[6-[(2-Chloro-6-methylphenyl)amino]imidzao[1,5-a]pyrido[3,2-e]pyrazin-2-yl]imino]bis[ethanol] | 3.635 |
| 125 | HOCH₂CH₂-NH-X₁ | 2,6-dimethylphenyl-NH-X₂ | 2-[[6-[(2,6-Dimethylphenyl)amino]imidazo[1,5-a]pyrido[3,2-e]pyrazin-2-yl]amino]ethanol | 2.478 |
| 126 | HOCH₂CH₂-N(CH₃)-X₁ | 2,6-dimethylphenyl-NH-X₂ | 2-[[6-(2,6-Dimethylphenyl)amino]imidazo[1,5-a]pyrido[3,2-e]pyrazin-2-yl]methykamino]ethanol | 2.687 |

TABLE 4-continued

| Ex. No | R₁ | R₂ | Compound name | HPLC time (min) |
|---|---|---|---|---|
| 127 | HOCH₂CH₂-N(X₁)-CH₂CH₂OH | 2,6-dimethylphenyl-NH-X₂ | 2,2'-[[6-[(2,6-Dimethylphenyl)amino]imidazo[1,5-a]pyrdio[3,2-e]pyrazin-2-yl]imino]bis[ethanol] | 2.440 |
| 128 | HOCH₂-CH(OH)-CH₂-NH-X₁ | 2,6-dimethylphenyl-NH-X₂ | 3-[[6-[2,6-Dimethylphenyl)amino]imidzao[1,5-a]pyrido[3,2-e]pyrazin-2-yl]amino]-1,2-propanediol | 2.349 |
| 129 | HOCH₂-CH(OH)-CH₂-N(CH₃)-X₁ | 2,6-dimethylphenyl-NH-X₂ | 2-[[6-[(2,6-Dimethylphenyl)amino]imidazo[1,5-a]pyrido[3,2-e]pyrazin-2-yl]methylamino]-1,2-propanediol | 2.587 |
| 130 | HOCH₂-CH(NH-X₁)-CH₂OH | 2-chloro-6-methylphenyl-NH-X₂ | 2-[[6-[(2-Chloro-6-fluorophenyl)amino]imidazo[1,5-a]pyrido[3,2-e]pyrazin-2-yl]amino]-1,3-propanediol | 2.490 |
| 131 | (R)-prolinamide N-X₁ | 2-chloro-6-methylphenyl-NH-X₂ | (R)-1-[6-[(2-Chloro-6-methylphenyl)amino]imidazo[1,5-a]pyrido[3,2-e]pyrazin-2-yl-]-2-pyrrolidinecarboxamide | 2.754 |
| 132 | (CH₃)₂N-CH₂CH₂-NH-X₁ | 2-chloro-6-methylphenyl-NH-X₂ | N⁶-(2-Chloro-6-methylphenyl)-N²-[2-(dimethylamino)ethyl]imidazo[1,5-a]pyrido[3,2-e]pyrazine-2,6-diamine | 2.057 |
| 133 | (CH₃)₂N-CH₂CH₂-N(CH₃)-X₁ | 2-chloro-6-methylphenyl-NH-X₂ | N⁶-(2-Chloro-6-methylphenyl)-N²-[2-(dimethylamino)ethyl]-N²-methylimidazo[1,5-a]pyrido[3,2-e]pyrazine-2,6-diamine | 2.215 |
| 134 | (CH₃)₂N-CH₂CH₂-NH-X₁ | 2,6-dimethylphenyl-NH-X₂ | N⁶-(2,6-Dimethylphenyl)-N²-[2-(dimethylamino)ethyl]imidazo[1,5-a]pyrido[3,2-e]pyrazine-2,6-diamine | 1.853 |

TABLE 4-continued

| Ex. No | R₁ | R₂ | Compound name | HPLC time (min) |
|---|---|---|---|---|
| 135 | (CH₃)₂N-CH₂CH₂-N(CH₃)-X₁ | X₂-N(2,6-dimethylphenyl) | N²-[2-(Dimethylamino)ethyl]-N⁶-(2,6-dimethylphenyl)-N²-methylimidazo[1,5-a]pyrido[3,2-e]pyrazine-2,6-diamine | 1.954 |
| 136 | (3,4-dihydroxypyrrolidin-1-yl)-X₁ | X₂-N(2,6-dimethylphenyl) | (2S-trans)-1-[6-[(2,6-Dimethylphenyl)amino]imidazo[1,5-a]pyrido[3,2-e]pyrazin-2-yl]-3,4-pyrrolidinediol | 2.647 |
| 137 | thiomorpholin-4-yl-X₁ | X₂-N(2-chloro-6-methylphenyl) | 6-(2-Chloro-6-methylphenyl)-2-(4-thiomorpholinyl)imidazo[1,5-a]pyrido[3,2-e]pyrazin-6-amine | 3.575 |
| 138 | HOCH₂-CH(OH)-CH₂-N(CH₃)-X₁ | X₂-N(2,6-dimethylphenyl) | (S)-3-[[6-[(2,6-Dimethlphenyl)amino]imidazo[1,5-a]pyrido[3,2-e]pyrazin-2-yl]methylamino]-1,2-propanediol | 2.587 |
| 139 | HOCH₂CH₂-NH-CH₂CH₂-N(CH₃)-X₁ | X₂-N(2,6-dimethylphenyl) | 2-[[2-[[6-[(2,6-Dimethylphenyl)amino]imidazo[1,5-a]pyrido[3,2-e]pyrazin-2-yl]methylamino]ethyl]amino]ethanol | 2.004 |
| 140 | thiomorpholin-4-yl-X₁ | X₂-N(2,6-dimethylphenyl) | 6-(2,6-Dimethylphenyl)-2-(4-thiomorpholinyl)imidazo[1,5-a]pyrido[3,2-e]pyrazin-6-amine | 3.276 |
| 141 | (HOCH₂)₂C(CH₃)-NH-X₁ | X₂-N(2-chloro-6-methylphenyl) | 2-[[6-[(2-Chloro-6-methylphenyl)amino]imidazo[1,5-a]pyrido[3,2-e]pyrazin-2-yl]amino]-2-methyl-1,3-propanediol | 2.670 |
| 142 | (3,4-dihydroxypyrrolidin-1-yl)-X₁ | X₂-N(2-chloro-6-methylphenyl) | (3R-trans)-1-[6-[(2-Chloro-6-methylphenyl)amino]imidazo[1,5-a]pyrido[3,2-e]pyrazin-2-yl]-3,4-pyrrolidinediol | 2.509 |

TABLE 4-continued

| Ex. No | R₁ | R₂ | Compound name | HPLC time (min) |
|---|---|---|---|---|
| 143 | (pyrrolidine with 3,4-diol, N-X₁) | 2,6-dimethylphenyl-NH-X₂ | (3R-trans)-1-[6-[(2,6-Dimethylphenyl)amino]imidazo[1,5-a]pyrido[3,2-e]pyrazin-2-yl]-3,4-pyrrolidinediol | 2.357 |
| 144 | HOCH₂-CH(OH)-CH₂-NH-X₁ | 2-chloro-6-methylphenyl-NH-X₂ | 3-[[6-[(2-Chloro-6-methylphenyl)amino]imidazo[1,5-a]pyrido[3,2-e]pyrazin-2-yl]amino]-1,2-propanediol | 2.553 |
| 145 | HOCH₂-CH(OH)-CH₂-N(CH₃)-X₁ | 2-chloro-6-methylphenyl-NH-X₂ | 3-[[6-[(2-Chloro-6-methylphenyl)amino]imidazo[1,5-a]pyrido[3,2-e]pyrazin-2-yl]methylamino]-1,2-propanediol | 2.785 |
| 146 | 1-deoxy-D-glucitol-N(CH₃)-X₁ | 2-chloro-6-methylphenyl-NH-X₂ | 1-[[6-[(2-Chloro-6-methylphenyl)amino]imidazo[1,5-a]pyrido[3,2-e]pyrazin-2-yl]methylamino]-1-deoxy-D-glucitol | 2.594 |
| 147 | HO-CH₂CH₂-piperazine-X₁ | 2-chloro-6-methylphenyl-NH-X₂ | 4-[6-[(2-Chloro-6-methylphenyl)amino]imidazo[1,5-a]pyrido[3,2-e]pyrazin-2-yl]-1-piperazineethanol | 2.076 |
| 148 | HOCH₂-CH(OH)-CH₂-N(CH₃)-X₁ (S) | 2-chloro-6-methylphenyl-NH-X₂ | (S)-3-[[6-[(2-Chloro-6-methylphenyl)amino]imidazo[1,5-a]pyrido[3,2-e]pyrazin-2-yl]methylamino]-1,2-propanediol | 2.772 |
| 149 | 1-deoxy-D-glucitol-N(CH₃)-X₁ | 2,6-dimethylphenyl-NH-X₂ | 1-Deoxy-1-[[6-[(2,6-dimethylphenyl)amino]imidazo[1,5-a]pyrido[3,2-e]pyrazin-2-yl]methylamino]-D-glucitol | 2.446 |
| 150 | HO-CH₂CH₂-piperazine-X₁ | 2,6-dimethylphenyl-NH-X₂ | 4-[6-[(2,6-Dimethylphenyl)amino]imidazo[1,5-a]pyrido[3,2-e]pyrazin-2-yl]-1-piperazineethanol | 1.839 |

TABLE 4-continued

| Ex. No | R₁ | R₂ | Compound name | HPLC time (min) |
|---|---|---|---|---|
| 151 | HO-CH₂CH₂-NH-CH₂CH₂-N(CH₃)-X₁ | X₂-N, H₃C, Cl (2-chloro-6-methylphenyl) | 2-[[2-[[6-[(2-Chloro-6-methylphenyl)amino]imidazo[1,5-a]pyrido[3,2-e]pyrazin-2-yl]methylamino]ethyl]amino]ethanol | 2.216 |
| 152 | HO-CH₂-CH(OH)-CH₂-N(CH₃)-X₁ | X₂-N, H₃C, Cl | (R)-3-[[6-[(2-Chloro-6-methylphenyl)amino]imidazo[1,5-a]pyrido[3,2-e]pyrazin-2-yl]methylamino]-1,2-propanediol | 2.818 |
| 153 | HO-CH₂-CH(OH)-CH₂-N(CH₃)-X₁ | X₂-N, H₃C, CH₃ | (R)-3-[[6-[(2,6-Dimethylphenyl)amino]imidazo[1,5-a]pyrido[3,2-e]pyrazin-2-yl]methylamino]-1,2-propanediol | 2.611 |
| 154 | H₃C-NH-CH₂CH₂-N(CH₃)-X₁ | X₂-N, H₃C, Cl | $N^6$-(2-Chloro-6-methylphenyl)-$N^2$-methyl-$N^2$-[2-(methylamino)ethyl]imidazo[1,5-a]pyrido[3,2-e]pyrazine-2,6-diamine | 2.215 |
| 155 | H₃C-NH-CH₂CH₂-N(CH₃)-X₁ | X₂-N, H₃C, CH₃ | $N^2$-(2,6-Dimethylphenyl)-$N^2$-methyl-$N^2$-[2-(methylamino)ethyl]imidazo[1,5-a]pyrido[3,2-e]pyrazine-2,6-diamine | 2.007 |
| 156 | O=S-thiomorpholine-N-X₁ | X₂-N, H₃C, Cl | N-(2-Chloro-6-methylphenyl)-2-(4-thiomorpholinyl)imidazo[1,5-a]pyrido[3,2-e]pyrazin-6-amine- 1-oxide | 2.664 |
| 157 | O=S-thiomorpholine-N-X₁ | X₂-N, H₃C, CH₃ | 6-(2,6-Dimethylphenyl)-2-(4-thiomorpholinyl)imidazo[1,5-a]pyrido[3,2-e]pyrazin-6-amine 1-oxide | 2.449 |
| 158 | piperazine-2-CH₂OH, N-X₁ | X₂-N, H₃C, Cl | 4-[6-[(2-Chloro-6-methylphenyl)amino]imidazo[1,5-a]pyrido[3,2-e]pyrazin-2-yl]-2-piperazinemethanol | 2.114 |

TABLE 4-continued

| Ex. No | R₁ | R₂ | Compound name | HPLC time (min) |
|---|---|---|---|---|
| 159 | piperazine with CH₂OH | 2,6-dimethylphenyl-NH-X₂ | 4-[6-[(2,6-Dimethylphenyl)amino]imidazo[1,5-a]pyrido[3,2-e]pyrazin-2-yl]-2-piperazinemethanol | 1.891 |
| 160 | HOCH₂-CH(OH)-CH₂-NH-X₁ | 2,6-dimethylphenyl-NH-X₂ | 3-[[6-[(2,6-Dimeythylphenyl)amino]imidazo[1,5-a]pyrido[3,2-e]pyrazin-2-yl]methylamino]1,2-propaneidol | 2.587 |
| 161 | (H₃CO)₂CH-CH₂-N-X₁ | 2-chloro-6-methylphenyl-NH-X₂ | N⁶-(2-Chloro-6-methylphenyl)-N²-(2,2-dimethoxyethyl)imidazo[1,5-a]pyrido[3,2-e]pyrazine-2,6-diamine | 3.010 |
| 162 | (R)-propanediol-piperazine-X₁ | 2-chloro-6-methylphenyl-NH-X₂ | (R)-3-[4-[6-[(2-Chloro-6-methylphenyl)amino]imidazo[1,5-a]pyrido[3,2-e]pyrazin-2-yl]-1-piperazinyl]-1,2-propanediol | 2.004 |
| 163 | (R)-propanediol-piperazine-X₁ | 2,6-dimethylphenyl-NH-X₂ | (R)-3-[4-[6-[(2,6-Dimethylphenyl)amino]imidazo[1,5-a]pyrido[3,2-e]pyrazin-2-yl]-1-piperazinyl]1,2-propanediol | 1.839 |
| 164 | (S)-piperazinemethanol-X₁ | 2-chloro-6-methylphenyl-NH-X₂ | (S)-4-[6-[(2-Chloro-6-methylphenyl)amino]imidazo[1,5-a]pyrido[3,2-e]pyrazin-2-yl]-2-piperazinemethanol | 2.091 |
| 165 | (S)-piperazinemethanol-X₁ | 2,6-dimethylphenyl-NH-X₂ | (S)-4-[6-[(2,6-Dimethylphenyl)amino]imidazo[1,5-a]pyrido[3,2-e]pyrazin-2-yl]-2-piperazinemethanol | 1.857 |

TABLE 4-continued

| Ex. No | R₁ | R₂ | Compound name | HPLC time (min) |
|---|---|---|---|---|
| 166 | (structure with OH, HN, piperazine-N-X₁) | (structure with X₂-N, H₃C, Cl phenyl) | (R)-4-[6-[(2-Chloro-6-methylphenyl)amino]imidazo[1,5-a]pyrido[3,2-e]pyrazin-2-yl]-2-piperazinemethanol | 2.082 |
| 167 | (structure with OH, HN, piperazine-N-X₁) | (structure with X₂-N, H₃C, CH₃ phenyl) | (R)-4-[6-[(2,6-Dimethylphenyl)amino]imidazo[1,5-a]pyrido[3,2-e]pyrazin-2-yl]-2-piperazinemethanol | 1.854 |
| 168 | (structure with HN, CH₃, H₃C, piperazine-N-X₁) | (structure with X₂-N, H₃C, Cl phenyl) | trans-N-(2-Chloro-6-methylphenyl)-2-(2,5-dimethyl-1-piperazinyl)imidazo[1,5-a]pyrido[3,2-e]pyrazin-6-amine | 2.357 |

EXAMPLE 169

Preparation of N-(2-Chloro-6-methylphenyl)-7-(1-piperazinyl)imidazo[1,5-a]pyrido[4,3-e]pyrazin-4-amine

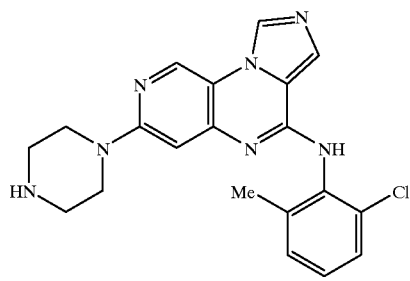

A. 2-Chloro-5-nitro-4-pyridinamine

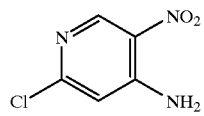

Compound 169A was prepared according to the literature, Robert J. Rousseau and Roland K. Robins, J. Heterocyclic Chem., (1965), Vol. 2, 196–201.

B. (2-Chloro-5-nitro-4-pyridinyl)carbamic acid 1,1-dimethylethyl ester

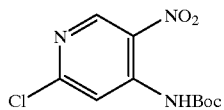

A mixture of 169A (995 mg, 5.75 mmol), di-tert-butyl dicarbonate (1.50 g, 6.90 mmol) and DMAP (140 mg, 1.15 mmol) in 60 mL of CH₂Cl₂ was stirred for 1 hr. The reaction mixture was diluted with CH₂Cl₂ and washed with 1 N HCl (2X), sat'd NaCl and dried over Na₂SO₄. Concentration in vacuo gave 1.54 g of 169B.

C. (5-Amino-2-chloro-4-pyridinyl)carbamic acid 1,1-dimethylethyl ester

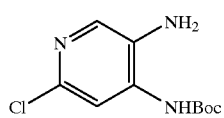

Compound 169B (1.54 g, 5.6 mmol) in 70 mL of MeOH containing 2.1 g of Raney Nickel was stirred under hydrogen atmosphere (Parr shaker, 40 psi) for 2.0 hrs. The catalyst was removed by filtration and the filtrate was concentrated in vacuo. Purification by flash chromatography (Hexane/EtOAc: 4:1) on silica gel gave 980 mg of 169C.

D. 2-[[6-Chloro-4-[[(1,1-dimethylethoxy)carbonyl]amino]-2-pyridinyl]amino]-2-methoxyacetic acid ethyl ester

A mixture of 169C (300 mg, 1.23 mmol) and ethyl glyoxylate (50% solution in toluene, 0.32 mL, 1.60 mmol) in MeOH was heated at 65° C. for 5 hrs. The reaction mixture was diluted with MeOH and the resulting precipitate was removed by filtration. The filtrate was concentrated in vacuo to give 435 mg of 169D as a yellow oil.

E. 3-[6-Chloro-4-[[(1,1-dimethylethoxy)carbonyl]amino]-2-pyridinyl]-3H-imidazole-4-carboxylic acid ethyl ester

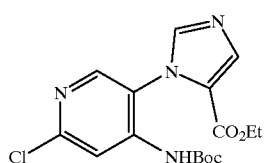

A mixture of 169D (435 mg, 1.22 mmol), tosylmethyl isocyanide (592 mg, 3.04 mmol) and solid $K_2CO_3$ (670 mg, 4.86 mmol) in 11 mL of EtOH was heated at 60° C. for 3 hrs. Water was added and the beige precipitate was collected by filtration, rinsed with more water. Drying under high vacuum gave 430 mg of 169E.

F. 7-Chloroimidazol[1,5-a]pyrido[4,3-e]pyrazine-4(5H)-one

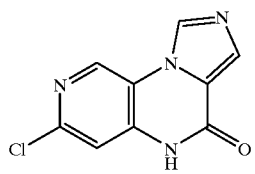

A mixture of 169E (430 mg) and trifluoroacetic acid (3 mL) was stirred for 15 min. Concentration in vacuo and the residue was taken in $CH_2Cl_2$, washed with Sat'd $NaHCO_3$, water, sat'd NaCl and dried over anhydrous $Na_2SO_4$. Flash chromatography (Hexane/EtOAc: 3:1) on silica gel gave 223 mg of intermediate as a yellow solid.

A mixture of above intermediate (830 mg, 3.12 mmol) and solid $K_2CO_3$ (760 mg, 5.5 mmol) in 35 mL of dry DMF was heated to reflux for 1.0 hr. Concentration in vacuo and followed by addition of AcOH to the residue (pH 7.0). The precipitate was collected by filtration, rinsed with water and dried under high vacuum to give 568 mg of 169F as a beige solid.

G. 4,7-Dichloroimidazo[1,5-a]pyrido[4,3-e]pyrazine

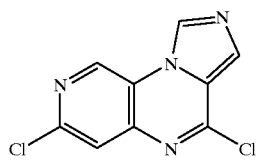

A mixture of 169F (341 mg, 1.55 mmol), $Et_3N$ (0.43 mL, 3.10 mmol) and $POCl_3$ (16 mL) was heated to reflux for 1.5 hrs. Reaction mixture was concentrated in vacuo, azeotropic evaporation several times with toluene and the residue was diluted with $CH_2Cl_2$ and half saturated $NaHCO_3$ at 0° C. Stirring was continued for 3 hrs. The organic layer was separated and dried over anhydrous $Na_2SO_4$. Concentration in vacuo followed by flash chromatography (Hexane-EtOAc: 75:35) on silica gel gave 260 mg of 169G as a beige solid.

H. 7-Chloro-N-(2-chloro-6-methylphenyl)imidazo[1,5-a]pyrido[4,3-e]pyrazin-4-amine Compound 169H was prepared by an analogous method to that of 7D.

I. N-(2-Chloro-6-methylphenyl)-7(1-piperazinyl)imidazol[1,5-a]pyrido[4,3-e]pyrazin-4-amine The title compound 169I was prepared by an analogous method to that of 8. HPLC ret. time: 2.276 min (method of Example 1).

EXAMPLES 170–171

Compounds 170–171 were prepared from Compound 169H by an analogous method as that of Compound 169I. These compounds have the structure shown below:

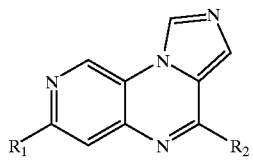

where $R_1$ and $R_2$ are defined in the following Table 5. The HPLC retention times of Table 5 were obtained by the method of Example 1. "$X_1$" and "$X_2$" in Table 5 are not substitutents, but rather show the point of attachment of $R_1$ and $R_2$, respectively, to the remainder of the compound of formula I. Unfilled valences on nitrogen indicate the presence of a hydrogen.

TABLE 5

| Ex. No | $R_1$ | $R_2$ | Compound name | HPLC time (min) |
|---|---|---|---|---|
| 170 | H₃C–N(CH₃)–CH₂CH₂–NH–X₁ | X₂–NH–(2-Cl-6-CH₃-C₆H₃) | $N^4$-(2-chloro-6-methylphenyl)-$N^7$-[2-(dimethylamino)ethyl]imidazo[1,5-a]pyrido[4,3-e]pyrazine-4,7-diamine | 2.211 |

TABLE 5-continued

| Ex. No | R₁ | R₂ | Compound name | HPLC time (min) |
|---|---|---|---|---|
| 171 | [morpholine-CH₂CH₂-NH-X₁ structure] | [X₂-N, 2-chloro-6-methylphenyl structure] | $N^4$-(2-Chloro-6-methylphenyl)-$N^7$-[2-(4-morpholinyl)ethyl]imidazo[1,5-a]pyrido[4,3-e]pyrazine-4,7-diamine | 2.225 |

EXAMPLE 172

Preparation of (S)-N-(2-Chloro-6-methylphenyl)-8-(3-methyl-1-piperazinyl)imidazo[1,5-a]pyrido[3,4-e]pyrazin-4-amine A. 4,6-Dichloro-3-pyridinecarboxylic acid Compound 172A was prepared according to the literature, A. Albert and G. B. Barlin, *J. Chem. Soc.*, (1963), 5156–5166.

B. 4,6-Dichloro-3-pyridinamine

To a solution of 172A (192 mg, 1.0 mmol) in 1.0 mL of dry DMF cooled at 0° C. was added triethylamine (0.14 mL, 1.0 mmol), followed by diphenylphosphoryl azide (0.216 mL, 1.0 mL). The mixture was stirred at ambient temperature for 1.0 hr and poured into a mixture of ice-water-EtOAc. The reaction mixture was extracted with EtOAc (x2) and combined extracts washed with water, sat'd NaHCO₃, sat'd NaCl and dried over Na₂SO₄. Concentration in vacuo gave 217 mg of light tan solid.

Above solid was dissolved in 2.5 mL of dry toluene and heated to reflux. A solution of tert-butyl alcohol in 1.0 mL of dry toluene was added and the mixture was heated at 90–95° C. for 4.0 hrs. Concentration in vacuo followed by flash chromatography (hexane-EtOAc: 95:5) on silica gel gave 168 mg of colorless oil.

Above material was treated with trifluoroacetic acid (1.5 mL) and CH₂Cl₂ (0.5 mL). Concentrated in vacuo and residue was extracted with CH₂Cl₂ (x2) and combined extracts washed with water, sat'd NaHCO₃, sat'd NaCl and dried over Na₂SO₄. Concentration in vacuo gave 104 mg of 172B as a white solid.

C. N-(4,6-Dichloro-3-pyridinyl)-1H-imidazole-4-carboxamide

Compound 172C was prepared from 172B by an analogous method as that of 7A.

D. 8-Chloroimidazo[1,5-a]pyrido[3,4-e]pyrazin-4(5H)-one

Compound 172D was prepared from 172C by an analogous method as that of 7B, except that K₂CO₃ was replaced with DBU, dimethylacetamide was replaced with DMF, and the mixture was heated at 150–160° C. for 1.0 hour.

E. 4,8-Dichloroimidazo[1,5-a]pyrido[3,4-e]pyrazine

Compound 172E was prepared from 172D by an analogous method as that of 7C.

F. 8-Chloro-N-(2-chloro-6-methylphenyl)imidazo[1,5-a]pyrido[3,4-e]pyrazin-4-amine

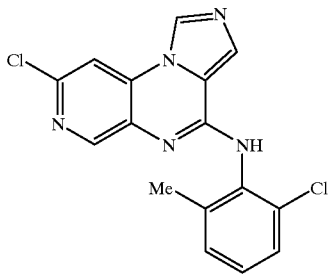

Compound 172F was prepared from 172E by an analogous method as that of 7D.

G. (S)-N-(2-Chloro-6-methylphenyl)-8-(3-methyl-1-piperazinyl)imidazo[1,5-a]pyrido[3,4-e]pyrazin-4-amine The title compound 172G was prepared from 172F by an analogous method as that 8. HPLC ret. time: 2.304 min (method of Example 1).

EXAMPLE 173

Preparation of cis-N-(2-Chloro-6-methylphenyl)-8-(3,5-dimethyl-1-piperazinyl)imidazo[1,5-a]pyrido[3,4-e]pyrazin-4-amine

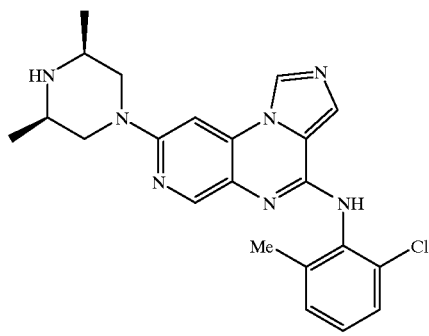

Compound 173 was prepared from 172F by an analogous method as that of 8. HPLC ret. time: 2.404 min (method of Example 1).

EXAMPLE 174

Preparation of N-Butyl-N'-[6-[(2,6-dimethylphenyl)amino]imidazo[1,5-a]pyrido[3,2-e]pyrazin-9-yl]urea

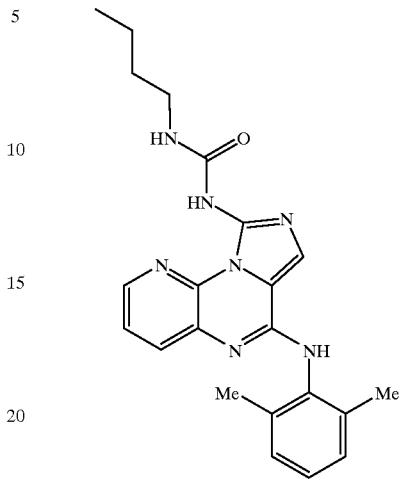

A. (9-Chloroimidazo[1,5-a]pyrido[3,2-e]pyrazin-6-yl)(2,6-dimethylphenyl)carbamic acid 1,1-dimethylethyl ester

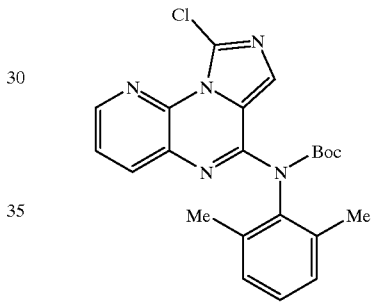

To a solution of Compound 6 (1.8 g, 6.22 mmol) in 120 mL of $CH_2Cl_2$ was added sodium bis(trimethylsilyl)amide (7.5 mL, 7.46 mmol, 1.0M solution in THF). After 20 min, di-tert-butyl dicarbonate (2.03 g, 9.34 mmol) was added, followed by DMAP (152 mg, 1.24 mmol). The reaction mixture was stirred for 2.0 hrs, diluted with $CH_2Cl_2$ and washed with 1 N HCl (2X), water, sat'd NaCl and dried over $Na_2SO_4$. Concentration in vacuo followed by flash chromatography (Hexane-EtOAc: 4:1) on silica gel gave 1.65 g of intermediate.

To a solution of above prepared intermediate (1.2 g, 3.08 mmol) in 30 mL of dry THF cooled at −78° C. was added a solution of LDA (2.78 mL, 5.55 mmol, 2.0M in THF). After 20 min, a solution of N-chlorosuccinimide (1.64 g, 12.32 mmol) in 30 mL of dry THF was added in one portion and stirring was continued for another 2.0 hrs at −78° C.,

87 then room temperature overnight. CH$_2$Cl$_2$ was added and the mixture was washed with 1 N HCl (2X), water, sat'd NaCl and dried over Na$_2$SO$_4$. Concentration in vacuo followed by flash chromatography (Hexane-EtOAc: 4:1) on silica gel gave 0.68 g of Compound 174A as a light brown solid.

B. N6-(2,6-Dimethylphenyl)-N9-[(4-methoxyphenyl)methyl]imidazo[1,5-a]pyrido[3,2-e]pyrazine-6,9-diamine

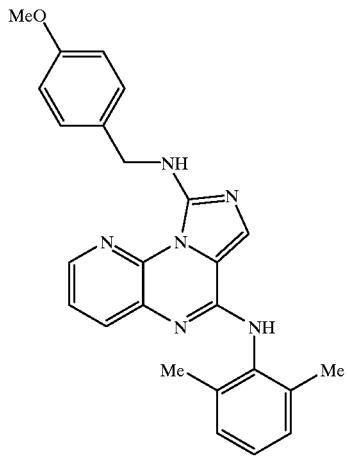

A mixture of 174A (220 mg, 0.52 mmol) and 4-methoxybenzylamine (5 mL) was heated at 160° C. for 5 hrs. The reaction mixture was poured into a mixture of EtOAc-water. The organic layer was washed with sat'd NH$_4$Cl, water, sat'd NaCl and dried over anhydrous Na$_2$SO$_4$. Concentration in vacuo followed by flash chromatography (Hexane-EtOAc: 4:1) on silica gel gave 70 mg of Compound 174B as a brown solid.

C. N-Butyl-N'-[6-[(2,6-dimethylphenyl)amino]imidazo[1,5-a]pyrido[3,2-e]pyrazin-9-yl]-Ni-[(4-methoxyphenyl)methyl]urea

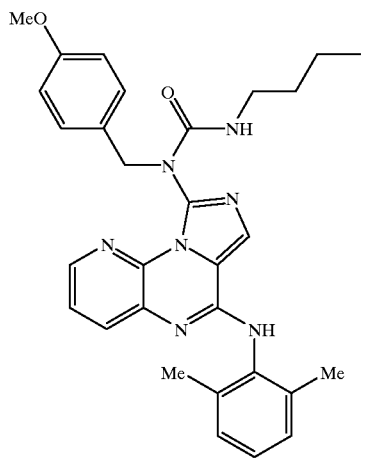

88

A mixture of 174B (35 mg, 0.083 mmol) and n-butyl isocyanate (0.014 mL, 0.123 mmol) in 1.5 mL of dry THF containing 0.5 mL of dry pyridine was stirred for 3.0 hrs at 50° C. The volatile was removed under reduced pressure and the residue taken into CH$_2$Cl$_2$. The reaction mixture was washed with 1 N HCl (2X), water, sat'd NaCl and dried over Na$_2$SO$_4$. Concentration in vacuo gave a crude produce which was used immediately in next reaction.

D. N-Butyl-N'-[6-[(2,6-dimethylphenyl)amino]imidazo[1,5-a]pyrido[3,2-e]pyrazin-9-yl]urea The mixture of 174C and trifluoroacetic acid (1.5 mL) was heated at 50° C. overnight. Concentration in vacuo and the mixture was washed with sat'd NaHCO$_3$, water, sat'd NaCl and dried over Na$_2$SO$_4$. Concentration in vacuo followed by flash chromatography (Hexane-EtOAc: 3:2) on silica gel gave 10 mg of titled compound as a light brown solid. HPLC ret. time: 3.540 min (method of Example 1).

EXAMPLES 175–177

Compounds 175–177 were prepared, from 174B, by an analogous method to that of 174D. These compounds have the structure shown below:

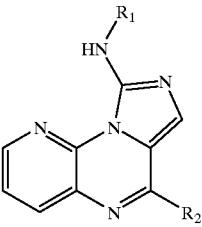

where R$_1$ and R$_2$ are defined in the following Table 6. The HPLC retention times of Table 6 were obtained by the method of Example 1. "X$_1$" and "X$_2$" in Table 6 are not substitutents, but rather show the point of attachment of R$_1$ and R$_2$, respectively, to the remainder of the compound of formula I. Unfilled valences on nitrogen indicate the presence of a hydrogen.

TABLE 6

| Ex. No | R₁ | R₂ | Compound name | HPLC time (min) |
|---|---|---|---|---|
| 175 | benzyl-NH-C(O)-X₁ | X₂-NH-(2,6-dimethylphenyl) | N-[6-[(2,6-Dimethylphenyl)amino]imidazo[1,5-a]pyrido[3,2-e]pyrazin-9-yl]-N'-(phenylmethyl)urea | 3.633 |
| 176 | propyl-NH-C(O)-X₁ | X₂-NH-(2,6-dimethylphenyl) | N-[6-[(2,6-Dimethylphenyl)amino]imidazo[1,5-a]pyrido[3,2-e]pyrazin-9-yl]-N'-propylurea | 3.320 |
| 177 | isopropyl-NH-C(O)-X₁ | X₂-NH-(2,6-dimethylphenyl) | N-[6-[(2,6-Dimethylphenyl)amino]imidazo[1,5-a]pyrido[3,2-e]pyrazin-9-yl]-N'-(1-methylethyl)urea | 3.427 |

What is claimed is:

1. A compound of the following formula I or a salt thereof:

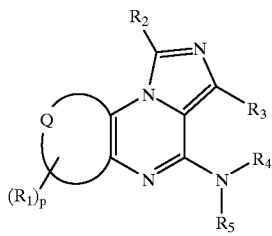

(I)

where

Q, together with the atoms to which it is bonded, forms a 5-, 6- or 7-membered heterocyclic ring;

p is 0 or an integer from 1 to t, where t=3 when Q forms a 5-membered ring, t=4 when Q forms a 6-membered ring, and t=5 when Q forms a 7-membered ring;

each $R_1$, and $R_2$ and $R_3$, are independently selected from:
  (1) hydrogen or $R_6$, where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
  (2) —OH or —$OR_6$;
  (3) —SH or —$SR_6$;
  (4) —$C(O)_qH$, —$C(O)_qR_6$, or —O—$C(O)_qR_6$, where q is 1 or 2;
  (5) —$SO_3H$ or —$S(O)_qR_6$;
  (6) halo;
  (7) cyano;
  (8) nitro;
  (9) —$Z_4$—$NR_7R_8$;
  (10) —$Z_4$—$N(R_9)$—$Z_5$—$NR_{10}R_{11}$;
  (11) —$Z_4$—$N(R_{12})$—$Z_5$—$R_6$;
  (12) —$SiR_{13}R_{14}R_{15}$;
  (13) —$P(O)(OR_6)_2$;
  (14) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
  (15) any two groups $R_1$ may, together with the atoms to which they are attached, form a heterocyclo group, which group is unsubstituted or substituted with $Z_1$, $Z_2$ and $Z_3$;

$R_4$ and $R_5$:
  (1) are each independently hydrogen, $R_6$, or —$C(O)R_6$; or
  (2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$:
  (1) are each independently hydrogen or $R_6$;
  (2) $R_7$ and $R_8$ may together by alkylene or alkenylene, completing a 3- to 8-membered saturated or unsaturated ring with the nitrogen atom to which they are attached, which ring is unsubstituted or substituted with $Z_1$, $Z_2$ and $Z_3$; or
  (3) any two of $R_9$, $R_{10}$ and $R_{11}$ may together by alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
  (1) alkyl; or
  (2) phenyl;

$Z_1$, $Z_2$ and $Z_3$ are each independently:
  (1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —C(O)$_q$H, —C(O)$_q Z_6$, or —O—C(O)$_q Z_6$;
(5) —SO$_3$H or —S(O)$_q Z_6$;
(6) halo;
(7) cyano;
(8) nitro;
(9) —$Z_4$—$NZ_7 Z_8$;
(10) —$Z_4$—N($Z_9$)—$Z_5$—$NZ_7 Z_8$;
(11) —$Z_4$—N($Z_{10}$)—$Z_5$—$Z_6$;
(12) —$Z_4$—N($Z_{10}$)—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—(CH$_2$)$_q$—O—;
$Z_4$ and $Z_5$ are each independently:
(1) a single bond;
(2) —$Z_{11}$—S(O)$_q$—$Z_{12}$—;
(3) —$Z_{11}$—C(O)—$Z_{12}$—;
(4) —$Z_{11}$—C(S)—$Z_{12}$;
(5) —$Z_{11}$—O—$Z_{12}$—;
(6) —$Z_{11}$—S—$Z_{12}$—;
(7) —$Z_{11}$—O—C(O)—$Z_{12}$—; or
(8) —$Z_{11}$—C(O)—O—$Z_{12}$—;
$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- or 8-membered saturated or unsaturated ring together with the nitrogen atoms to which they are attached, which ring is unsubstituted or substituted with $Z_1$, $Z_2$ and $Z_3$; and
$Z_{11}$ and $Z_{12}$ are each independently:
(1) a single bond;
(2) alkylene;
(3) alkenylene; or
(4) alkynylene.

2. A compound of claim 1, wherein Q, together with the atoms to which it is bonded, forms a heterocyclic ring selected from the group consisting of pyridine, pyrimidine, pyrazole and imidazole.

3. A compound of claim 1, wherein Q, together with the atoms to which it is bonded, forms pyridine.

4. A compound of claim 1, wherein p is 0, 1 or 2.

5. A compound of claim 1, wherein each $R_1$ is independently selected from hydrogen; —$OR_6$; —$Z_4$—$NR_7 R_8$; —$Z_4$—N($R_{12}$)—$Z_5$—$R_6$; alkoxy; nitro; halo; or alkyl, aryl or heterocyclo, each of which is unsubstituted or substituted with $Z_1$, $Z_2$ and $Z_3$.

6. A compound of claim 1, wherein $R_2$ is hydrogen, —$Z_4$—N($R_9$)—$Z_5$—$NR_{10}R_{11}$, or alkyl, where alkyl is unsubstituted or substituted with $Z_1$, $Z_2$ and $Z_3$.

7. A compound of claim 1, wherein $R_3$ is hydrogen or alkyl.

8. A compound of claim 1, wherein one of $R_4$ or $R_5$ is hydrogen, and wherein the other of $R_4$ or $R_5$ is phenyl substituted with $Z_1$, $Z_2$ and one or two groups $Z_3$.

9. A compound of claim 1, which compound of the formula I or salt thereof is selected from the group consisting of:
N-(2-Chloro-6-methylphenyl)imidazo[1,5-a]pyrido[3,2-e]pyrazin-6-amine;
N-(2-Bromophenyl)imidazo[1,5-a]pyrido[3,2-e]pyrazin-6-amine;
N-(2-Chloro-4,6-dimethylphenyl)imidazol[1,5-a]pyrido[3,2-e]pyrazin-6-amine;
N-(4-Bromo-2,6-dimethylphenyl)imidazo[1,5-a]pyrido[3,2-e]pyrazin-6-amine;
N-(2,4,6-Trimethylphenyl)imidazo[1,5-a]pyrido[3,2-e]pyrazin-6-amine;
N-(2,6-Dimethylphenyl)imidazo[1,5-a]pyrido[3,2-e]pyrazin-6-amine;
2-Chloro-N-(2-chloro-6-methylphenyl)imidazo[1,5-a]pyrido[3,2-e]pyrazin-6-amine;
N-(2-Chloro-6-methylphenyl)-2-(4-methyl-1-piperazinyl)imidazo[1,5-a]pyrido[3,2-e]pyrazin-6-amine;
N-(2-Chloro-6-methylphenyl)-2-(4-morpholinyl)imidazo[1,5-a]pyrido[3,2-e]pyrazin-6-amine;
$N^6$-(2-Chloro-6-methylphenyl)-$N^2$-[2-(4-morpholinyl)ethyl]imidazo[1,5-a]pyrido[3,2-e]pyrazine-2,6diamine;
N-(2-Chloro-6-methylphenyl)-2-[2-(4-morpholinyl)ethoxy]imidazo[1,5-a]pyrido[3,2-e]pyrazin-6-amine;
$N^6$-(2-6-methylphenyl)-$N^2$-(3-pyridinylmethyl)imidazo[1,5-a]pyrido[3,2-e]pyrazine-2,6-diamine;
N-(2-Chloro-6-methylphenyl)-2-(2-methoxyethoxy)imidazo[1,5-a]pyrido[3,2-e]pyrazin-6-amine;
N-(2-Chloro-6-methylphenyl)-2-(1-piperazinyl)imidazo[1,5-a]pyrido[3,2-e]pyrazin-6-amine;
N-(2-Chloro-6-methylphenyl)-2-(3,5-dimethyl-1-piperazinyl)imidazo[1,5-a]pyrido[3,2-e]pyrazin-6-amine;
N-(2-Chloro-6-methylphenyl)-2-[4-(2-pyridinyl)-1-piperazinyl]imidazo[1,5-a]pyrido[3,2-e]pyrazin-6-amine;
N-(2-Chloro-6-methylphenyl)-2-(4-(1-piperazinyl)imidazo[1,5-a]pyrido[3,2-e]pyrazin-6-amine;
N-(2-Chloro-6-methylphenyl)-2-(1-piperidinyl)imidazo[1,5-a]pyrido[3,2-e]pyrazin-6-amine;
2(4,1'-Bipiperidin-1-yl)-N-(2-chloro-6-methylphenyl)imidazo[1,5-a]pyrido[3,2e]pyrazin-6-amine;
N-(2-Chloro-6-methylphenyl)-2-(4-methyl-1-piperidinyl)imidazo[1,5-a]pyrido[3,2-e]pyrazin-6-amine;
$N^6$-(2-Chloro-6-methylphenyl)-$N^2$-methyl-$N^2$-(1-methyl-4-piperidinyl)imidazo[1,5-a]pyrido[3,2-e]pyrazine-2,6-diamine;
$N^6$-(2-Chloro-6-methylphenyl)-$N^2$-[2-(dimethylamino)ethyl]-$N^2$-ethylimidazo[1,5-a pyrido[3,2-e]pyrazine-2,6-diamine;
N-(2-Chloro-6-methylphenyl)-2-(1H-imidazol-1-yl)imidazo[1,5-a]pyrido[3,2-e]pyrazin-6-amine;
N-(2-Chloro-6-methylphenyl)-2-(4-ethyl-1-piperazinyl)imidazo[1,5-a]pyrido[3,2-e]pyrazin-6-amine;
N-(2-Chloro-6-methylphenyl)-2-(4-cyclohexyl-1-piperazinyl)imidazo[1,5-a]pyrido[3,2-e]pyrazin-6-amine;
$N^6$-(2-Chloro-6-methylphenyl)-$N^2$,$N^2$-dimethylimidazo[1,5-a]pyrido[3,2-e]pyrazine-2,6-diamine;
$N^6$-(2-Chloro-6-methylphenyl)-$N^2$, $N^2$-diethylimidazo[1,5-a]pyrido[3,2-e]pyrazine-2,6-diamine;
$N^2$-Butyl-$N^6$-(2-chloro-6-methylphenyl)-$N^2$-methylimidazo[1,5-a]pyrido[3,2-pyrazine-2,6-diamine;
2-Chloro-N-(2,6-dichlorophenyl)imidazo[1,5-a]pyrido[3,2-e]pyrazin-6-amine;
N-(2,6-Dichlorophenyl)-2-(4-methyl-1-piperazinyl)imidazo[1,5-a]pyrido[3,2-e]pyrazin-6-amine;

N-(2,6-Dichlorophenyl)-2-(1-piperazinyl)imidazo[1,5-a]
pyrido[3,2-e]pyrazin-6-amine;
N-(2,6-Dichlorophenyl)-2-(3,5-dimethyl-1-piperazinyl)
imidazo[1,5-a]pyrido[3,2-e]pyrazin-6-amine;
$N^6$-(2,6-Dichlorophenyl)-$N^2$,$N^2$-dimethylimidazo[1,5-a]
pyrido[3,2-e]pyrazine-2,6-diamine;
$N^6$-(2-Chloro-6-methylphenyl)-$N^2$-methylimidazo[1,5-a]
pyrido[3,2-e]pyrazine-2,6-diamine;
N-(2,6-Dichlorophenyl)-2-(4-morpholinyl)imidazo[1,5-a]
pyrido[3,2-e]pyrazin-6-amine;
$N^6$-(2,6-Dichlorophenyl)-$N^2$-methylimidazo[1,5-a]pyrido
[3,2-e]pyrazine-2,6-diamine;
$N^2$-(2-Aminoethyl)-$N^6$-(2-chloro-6-methylphenyl)imidazo
[1,5-a]pyrido[3,2-e]pyrazine-2,6-diamine;
$N^6$-(2-Chloro-6-methylphenyl)-$N^2$-(2-hydroxyethyl)
imidazo[1,5-a]pyrido[3,2-e]pyrazine-2,6-diamine;
N-(2-Chloro-6-methylphenyl)-2-[4-(2,2,2-trifluoroethyl)-1-
piperazinyl]imidazo[1,5-a]pyrido[3,2-e]pyrazin-6-amine;
N-(2,6-Dichlorophenyl)-2-[4-(2,2,2-trifluoroethyl)-1-
piperazinyl]imidazo[1,5-a]pyrido[3,2-e]pyrazin-6-amine;
$N^2$-(2-Aminoethyl)-$N^6$-(2,6-dichlorophenyl)imidazo[1,5-a]
pyrido[3,2-e]pyrazine-2,6-diamine;
N-(4-Bromo-2-chloro-6-methylphenyl)-2-(4-methyl-1-
piperazinyl)imidazo[1,5-a]pyrido[3,2-e]pyrazin-6-amine;
N-Cyclopropyl-3,5-dichloro-4-[[2-(4-methyl-1-piperazinyl)
imidazo[1,5-a]pyrido[3,2-e]pyrazin-6-yl]amino]
benzamide;
N-[1-[6-[(2-Chloro-6-methylphenyl)amino]imidazo[1,5-a]
pyrido[3,2-e]pyrazin-2-yl]-3-pyrrolidinyl]acetamide;
N-[1-[6-[(2-Chloro-6-methylphenyl)amino]imidazo[1,5-a]
pyrido[3,2-e]pyrazin-2-yl]-3-pyrrolidinyl]-N-
methylacetamide;
4-[6-[(2-Chloro-6-methylphenyl)amino]imidazo[1,5-a]
pyrido[3,2-e]pyrazin-2-yl]piperazinone;
1-Acetyl-4-[6-[(2-chloro-6-methylphenyl)amino]imidazo
[1,5-a]pyrido[3,2-e]pyrazin-2-yl]piperazine;
4-[6-[(2-Chloro-6-methylphenyl)amino]imidazo[1,5-a]
pyrido[3,2-e]pyrazin-2-yl]-1-(methylsulfonyl)piperazine;
4-[6-[(2-Chloro-6-methylphenyl)amino]imidazo[1,5-a]
pyrido[3,2-e]pyrazin-2-yl]-1-piperazinecarboxylic acid
methyl ester;
1-Acetyl-4-[6-[6-[(2,6-dichlorophenyl)amino]imidazo[1,5-
a]pyrido[3,2-e]pyrazin-2-yl]piperazine;
N-(2-Chloro-6-methylphenyl)imidazo[1,5-a]pyrido[2,3-e]
pyrazin-4-amine;
N-(2,6-Dimethylphenyl)imidazo[1,5-a]pyrido[2,3-e]
pyrazin-4-amine;
N-(2,6-Dimethylphenyl)imidazo[1,5-a]pyrido[3,4-e]
pyrazin-4-amine;
N-(2-Chloro-6-methylphenyl)imidazo[1,5-a]pyrido[3,4-e]
pyrazin-4-amine;
N-(2-Chloro-6-methylphenyl)-2-(hexahydro-1H-1,4-
diazepin-1-yl)imidazo[1,5-a]pyrido[3,2-e]pyrazin-6-
amine;
N-(2-Chloro-6-methylphenyl)-2-(hexahydro-4-methyl-1H-
1,4-diazepin-1-yl)imidazo[1,5-a]pyrido[3,2-e]pyrazin-6-
amine;
N-(2-Chloro-6-methylphenyl)-2-phenylimidazo[1,5-a]
pyrido[3,2-e]pyrazin-6-amine;
N-(2-Chloro-6-methylphenyl)-2-(4-methoxyphenyl)
imidazo[1,5-a]pyrido[3,2-e]pyrazin-6-amine;
N-(2-Chloro-6-methylphenyl)-3-methoxyimidazo[1,5-f]
pteridin-6-amine;
N-(2-Chloro-6-methylphenyl)-1,8-dimethyldiimidazo[1,5-
a:4',5'-e]pyrazin-5-amine;
N-(2-Chloro-6-methylphenyl)-1,3,8-trimethylimidazo[1,5-
a]pyrazolo[4,3-e]pyrazin-5-amine;

N-(2-Fluoro-6-methylphenyl)-2-(1-piperazinyl)imidazo[1,
5-a]pyrido[3,2-e]pyrazin-6-amine; and
2-(3,5-Dimethyl-1-piperazinyl)-N-(2-fluoro-6-
methylphenyl)imidazo[1,5-a]pyrido[3,2-e]pyrazin-6-
amine;
N-(2-Chloro-6-fluorophenyl)-2-(4-methyl-1-piperazinyl)
imidazo[1,5-a]pyrido[3,2-e]pyrazin-6-amine;
N-(2-Chloro-6-fluorophenyl)-2-(4-ethyl-1-piperazinyl)
imidazo[1,5-a]pyrido[3,2e]pyrazin-6-amine;
N-(2-Chloro-6-fluorophenyl)-2-(4-morpholinyl)imidazo[1,
5-a]pyrido[3,2-e]pyrazin-6amine;
N-(2-Chloro-6-fluorophenyl)-2-(2,6-dimethyl-4-
morpholinyl)imidazo[1,5-a]pyrido[3,2-e]pyrazin-6-
amine;
1-[6-[(2-Chloro-6-fluorophenyl)amino]imidazo[1,5-a]
pyrido[3,2-e]pyrazin-2-yl]-4-piperidinol;
N-(2-Chloro-6-fluorophenyl)-2-(hexahydro-4-methyl-1H-1,
4-diazepin-1-yl)imidazo[1,5-a]pyrido[3,2-e]pyrazin-6-
amine;
N-(2-Chloro-6-fluorophenyl)-2-(2,6-dimethyl-4-
morpholinyl)imidazo[1,5-a]pyrido[3,2-e]pyrazin-6-
amine;
1-[6-[(2-Chloro-6-methylphenyl)amino]imidazo[1,5-a]
pyrido[3,2-e]pyrazin-2-yl]-4-piperidinol;
N-(2-Chloro-6-methylphenyl)-2-methoxyimidazo[1,5-a]
pyrido[3,2-e]pyrazin-6-amine;
N-(2-Chloro-6-methylphenyl)-2-(hexahydro-1H-1,4-
diazepin-1-yl)imidazo[1,5-a]pyrido[3,2-e]pyrazin-6-
amine;
4-[6-[(2-Chloro-6-fluorophenyl)amino]imidazo[1,5-a]
pyrido[3,2-e]pyrazin-2-yl]-1-piperazineethanol;
N-(2-Chloro-6-fluorophenyl)-2-[4-[2-(4-morpholinyl)
ethyl]-1-piperazinyl]imidazo[1,5-a]pyrido[3,2-e]pyrazin-
6-amine;
N-(2-Chloro-6-fluorophenyl)-2-[4-(2-methoxyethyl)-1-
piperazinyl]imidazo[1,5-a]pyrido[3,2-e]pyrazin-6-amine;
N-(2-Chloro-6-fluorophenyl)-2-[4-(2-methoxyethyl)-1-
piperazinyl]imidazo[1,5-a]pyrido[3,2-e]pyrazin-6-amine;
N-(2-Chloro-6-fluorophenyl)-2-[4-[2-(dimethylamino)
ethyl]-1-piperazinyl]imidazo[1,5-a]pyrido[3,2-e]pyrazin-
6-amine;
N-(2-Chloro-6-methylphenyl)-2-[4-(2-methoxyethyl)-1-
piperazinyl]imidazo[1,5-a]pyrido[3,2-e]pyrazin-6amine;
N-(2-Chloro-6-methylphenyl)-2-[4-[2-(dimethylamino)
ethyl]-1-piperazinyl]imidazo[1,5-a]pyrido[3,2-e]pyrazin-
6-amine;
N-(2-Chloro-6-methylphenyl)-2-[4-[3-(dimethylamino)
propyl]-1-piperazinyl]imidazo[1,5-a]pyrido[3,2-e]
pyrazin-6-amine;
N-(2-Chloro-6-methylphenyl)-2-[4-[2-(4-morpholinyl)
ethyl]-1-piperazinyl]imidazo[1,5-a]pyrido[3,2-e]pyrazin-
6-amine;
(S)-N-(2-Chloro-6-fluorophenyl)-2-(3-methyl-1-
piperazinyl)imidazo[1,5-a]pyrido[3,2-e]pyrazin-6-amine;
(R)-N-(2-Chloro-6-fluorophenyl)-2-(3-methyl-1-
piperazinyl)imidazo[1,5-a]pyrido[3,2-e]pyrazin-6-amine;
(S)-N-(2-Chloro-6-methylphenyl)-2-(3-methyl-1-
piperazinyl)imidazo[1,5-a]pyrido[3,2-e]pyrazin-6-amine;
(R)-N-(2-Chloro-6-methylphenyl)-2-(3-methyl-1-
piperazinyl)imidazo[1,5-a]pyrido[3,2-e]pyrazin-6-amine;
(S)-N-(2,6-Dimethylphenyl)-2-(3-methyl-1-piperazinyl)
imidazo[1,5-a]pyrido[3,2-e]pyrazin-6-amine;
(R)-N-(2,6-Dimethylphenyl)-2-(3-methyl-1-piperazinyl)
imidazo[1,5-a]pyrido[3,2-e]pyrazin-6-amine;
N-(2,6-Dimethylphenyl)-2-(3,5-dimethyl-1-piperazinyl)
imidazo[1,5-a]pyrido[3,2-e]pyrazine-6-amine;
N-(2,6-Dimethylphenyl)-2-(1-piperazinyl)imidazo[1,5-a]
pyrido[3,2-e]pyrazin-6-amine;

2-[4-[2-(Dimethylamino)ethyl]-1-piperazinyl]-N-(2,6-dimethylphenyl)imidazo[1,5-a]pyrido[3,2-e]pyrazin-6-amine;
N(2,6-Dimethylphenyl)-2-(4-methyl-1-piperazinyl)imidazo[1,5-a]pyrido[3,2-e]pyrazin-6-amine;
N-(2,6-Dimethylphenyl)-2-(hexahydro-1H-1,4-diazepin-1-yl)imidazo[1,5-a]pyrido[3,2-e]pyrazin-6-amine;
N-(2,6-Dimethylphenyl)-2-(hexahydro-4-methyl-1H-1,4-diazepin-1-yl)imidazo[1,5-a]pyrido[3,2-e]pyrazin-6-amine;
(R)-1-[6-[(2,6-Dimethylphenyl)amino]imidazo[1,5-a]pyrido[3,2-e]pyrazin-2-yl]-3-pyrrolidinol;
(S)-1-[6-[(2,6-Dimethylphenyl)amino]imidazo[1,5-a]pyrido[3,2-e]pyrazin-2-yl]-3-pyrrolidinol;
(R)-1-[6-[(2-Chloro-6-methylphenyl)amino]imidazo[1,5-a]pyrido[3,2-e]pyrazin-2-yl]-3-pyrrolidinol;
(R)-1-[6-[(2-Chloro-6-methylphenyl)amino]imidazo[1,5-a]pyrido[3,2-e]pyrazin-2-yl]-3-pyrrolidinol]carbamic acid 1,1-dimethylethyl ester;
(S)-1-[6-[(2-Chloro-6-methylphenyl)amino]imidazo[1,5-a]pyrido[3,2-e]pyrazin-2-yl]-3-pyrrolidinol]carbamic acid 1,1-dimethylethyl ester;
N-(2-Chloro-6-methylphenyl)-2-(1-pyrrolidinyl)imidazo[1,5-a]pyrido[3,2-e]pyrazin-6-amine;
1-[6-[(2-Chloro-6-methylphenyl)amino]imidazo[1,5-a]pyrido[3,2-e]pyrazin-2-yl]-3-pyrrolidinol;
(R)-2-(3-Amino-1-pyrrolidinyl)-N-(2-chloro-6-methylphenyl)imidazo[1,5-a]pyrido[3,2-e]pyrazin-6-amine;
(S)-2-(3-Amino-1-pyrrolidinyl)-N-(2-chloro-6-methylphenyl)imidazo[1,5-a]pyrido[3,2-e]pyrazin-6-amine;
(S)-N-(2-Chloro-6-methylphenyl)-2-[2-(methoxymethyl)-1-pyrrolidinyl]imidazo[1,5-a]pyrido[3,2-e]pyrazin-6-amine;
(R)-N-(2-Chloro-6-methylphenyl)-2-[2-(methoxymethyl)-1-pyrrolidinyl]imidazo[1,5-a]pyrido[3,2-e]pyrazin-6-amine;
1-[6-[(2-Chloro-6-methylphenyl)amino]imidazo[1,5-a]pyrido[3,2-e]pyrazin-2-yl]-3-pyrrolidinol;
N-(2-Chloro-6-methylphenyl)-2-(1,4-dioxa-8-azaspiro[4.5]decan-8-yl)imidazo[1,5-a]pyrido[3,2-3]pyrazin-6-amine;
(S)-N-(2-Chloro-6-methylphenyl)-2-[3-(dimethylamino)-1-pyrrolidinyl]imidazo[1,5-a]pyrido[3,2-e]pyrazin-6-amine;
1-[6-[(2-Chloro-6-methylphenyl)amino]imidazo[1,5-a]pyrido[3,2-e]pyrazin-2-yl]-4-piperidinecarboxamide;
(R)-1-[6-[(2-Chloro-6-methylphenyl)amino]imidazo[1,5-a]pyrido[3,2-e]pyrazin-2-yl]-2-pyrrolidinemethanol;
1-[6-[(2-Chloro-6-methylphenyl)amino]imidazo[1,5-a]pyrido[3,2-e]pyrazin-2-yl]-2-piperidinemethanol;
1-[6-[(2-Chloro-6-methylphenyl)amino]imidazo[1,5-a]pyrido[3,2-e]pyrazin-2-yl]-3-piperidinemethanol;
1-[6-[(2-Chloro-6-methylphenyl)amino]imidazo[1,5-a]pyrido[3,2-e]pyrazin-2-yl]-4-piperidinemethanol;
1-[6-[(2-Chloro-6-methylphenyl)amino]imidazo[1,5-a]pyrido[3,2-e]pyrazin-2-yl]-3-piperidinecarboxamide;
(S)-1-[6-[(2-Chloro-6-methylphenyl)amino]imidazo[1,5-a]pyrido[3,2-e]pyrazin-2-yl]-2-pyrrolidinecarboxamide;
(R)-1-[6-[(2-Chloro-6-methylphenyl)amino]imidazo[1,5-a]pyrido[3,2-e]pyrazin-2-yl]-3-pyrrolidinol;
(R)-$N^6$-(2-Chloro-6-methylphenyl)-$N^2$-[1-(phenylmethyl)-3-pyrrolidinyl]imidazo[1,5-a]pyrido[3,2-e]pyrazine-2,6-diamine;
(S)-$N^6$-(2-Chloro-6-methylphenyl)-$N^2$-[1-(phenylmethyl)-3-pyrrolidinyl]imidazo[1,5-a]pyrido[3,2-e]pyrazine-2,6-diamine;
N-(2-Chloro-6-methylphenyl)-2-(4-methyl-1H-imidazol-1-yl)imidazo[1,5-a]pyrido[3,2-e]pyrazin-6-amine;
(R)-$N^6$-(2-Chloro-6-methylphenyl)-$N^2$-(3-pyrrolidinyl)imidazo[1,5-a]pyrido[3,2-e]pyrazine-2,6-diamine;
(S)-$N^6$-(2-Chloro-6-methylphenyl)-$N^2$-(3-pyrrolidinyl)imidazo[1,5-a]pyrido[3,2-e]pyrazine-2,6-diamine;
2-[[6-[(2-Chloro-6-methylphenyl)amino]imidazo[1,5-a]pyrido[3,2-e]pyrazin-2-yl]methylamino]ethanol;
2,2'-[[6-[(2-Chloro-6-methylphenyl)amino]imidazo[1,5-a]pyrido[3,2-e]pyrazin-2-yl]imino]bis[ethanol];
2-[[6-[(2,6-Dimethylphenyl)amino]imidazo[1,5-a]pyrido[3,2-e]pyrazin-2-yl]amino]ethanol;
2-[[6-[(2,6-Dimethylphenyl)amino]imidazo[1,5-a]pyrido[3,2-e]pyrazin-2-yl]methylamino]ethanol;
2,2'-[[6-[(2,6-Dimethylphenyl)amino]imidazo[1,5-a]pyrido[3,2-e]pyrazin-2-yl]imino]bis[ethanol];
3-[[6-[(2,6-Dimethylphenyl)amino]imidazo[1,5-a]pyrido[3,2-e]pyrazin-2-yl]amino]-1,2-propanediol;
3-[[6-[(2,6-Dimethylphenyl)amino]imidazo[1,5-a]pyrido[3,2-e]pyrazin-2-yl]methylamino]-1,2-propanediol;
2-[[6-[(2-Chloro-6-fluorophenyl)amino]imidazo[1,5-a]pyrido[3,2-e]pyrazin-2-yl]amino]-1,3-propanediol;
(R)-1-[6-[(2-Chloro-6-methylphenyl)amino]imidazo[1,5-a]pyrido[3,2-e]pyrazin-2-yl]-2-pyrrolidinecarboxamide;
$N^6$-(2-Chloro-6-methylphenyl)-$N^2$-[2-(dimethylamino)ethyl]imidazo[1,5-a]pyrido[3,2-e]pyrazine-2,6-diamine;
$N^6$-(2-Chloro-6-methylphenyl)-$N^2$-methylimidazo[1,5-a]pyrido[3,2-e]pyrazine-2,6-diamine;
$N^6$-(2,6-Dimethylphenyl)-$N^2$-[2-(dimethylamino)ethyl]imidazo[1,5-a]pyrido[3,2-e]pyrazine-2,6-diamine;
$N^6$-(2-Dimethylamino)ethyl]-$N^6$-(2,6-dimethylphenyl)-$N^2$-methylimidazo[1,5-a]pyrido[3,2-e]pyrazine-2,6-diamine;
(3S-trans)-1-[6-[(2,6-Dimethylphenyl)amino]imidazo[1,5-a]pyrido[3,2-e]pyrazine-2-yl]-3,4-pyrrolidinediol;
6-(2-Chloro-6-methylphenyl)-2-(4-thiomorpholinyl)imidazo[1,5-a]pyrido[3,2-e]pyrazin-6-amine;
(S)-3-[[6-[(2,6-Dimethylphenyl)amino]imidazo[1,5-a]pyrido[3,2-e]pyrazin-2-yl]methylamino]-1,2-propanediol;
2-[[2-[[6-[(2,6-Dimethylphenyl)aminolimidazo[1,5-a]pyrido[3,2-e]pyrazin-2-yl]methylamino]ethyl]amino]ethanol;
6-(2,6-Dimethylphenyl)-2-(4-thiomorpholinyl)imidazo[1,5-a]pyrido[3,2-e]pyrazin-6-amine;
2-[[6-[(2-Chloro-6-methylphenyl)amino]imidazo[1,5-a]pyrido[3,2-e]pyrazin-2-yl]amino]-2-methyl-1,3-propanediol;
(3R-trans)-1-[6-[(2-Chloro-6-methylphenyl)amino]imidazo[1,5-a]pyrido[3,2-e]pyrazin-2-yl]-3,4-pyrrolidinediol;
(3R-trans)-1-[6-[(2,6-Dimethylphenyl)amino]imidazo[1,5-a]pyrido[3,2-e]pyrazin-2-yl]-3,4-pyrrolidinediol;
(3R-trans)-1-[6-[(2,6-Dimethylphenyl)amino]imidazo[1,5-a]pyrido[3,2-e]pyrazin-2-yl]-3,4-pyrrolidinediol;
3-[[6-[(2-Chloro-6-methylphenyl)amino]imidazo[1,5-a]pyrido[3,2-e]pyrazin-2-yl]amino]-1,2-propanediol;
3-[[6-[(2-Chloro-6-methylphenyl)amino]imidazo[1,5-a]pyrido[3,2-e]pyrazin-2-yl]methylamino]-1,2-propanediol;
1-[[6-[(2-Chloro-6-methylphenyl)amino]imidazo[1,5-a]pyrido[3,2-e]pyrazin-2-yl]methylamino]-1-deoxy-D-glucitol;
4-[6-[(2-Chloro-6-methylphenyl)amino]imidazo[1,5-a]pyrido[3,2-e]pyrazin-2-yl]-1-piperazineethanol;
(S)-3-[[6-[(2-Chloro-6-methylphenyl)amino]imidazo[1,5-a]pyrido[3,2-e]pyrazin-2-yl]methylamino]-1,2-propanediol;
1-Deoxy-1-[[6-[(2,6-dimethylphenyl)amino]imidazo[1,5-a]pyrido[3,2-e]pyrazin-2-yl]methylamino]-D-glucitol;

4-[6-[(2,6-dimethylphenyl)amino]imidazo[1,5-a]pyrido[3,2-e]pyrazin-2-yl]-1-piperazineethanol;

2-[[2-[[6-[(2-Chloro-6-methylphenyl)amino]imidazo[1,5-a]pyrido[3,2-e]pyrazin-2-yl]methylamino]-ethyl]amino]ethanol;

(R)-3-[[6-[(2-Chloro-6-methylphenyl)amino]imidazo[1,5-a]pyrido[3,2-e]pyrazin-2-yl]methylamino]-1,2-propanediol;

(R)-3-[[6-[(2,6-Dimethylphenyl)amino]imidazo[1,5-a]pyrido[3,2-e]pyrazin-2-yl]methylamino]-1,2-propanediol;

$N^6$-(2-Chloro-6-methylphenyl)-$N^2$-methyl-$N^2$-[2-(methylamino)ethyl]imidazo[1,5-a]pyrido[3,2-e]pyrazine-2,6-diamine;

$N^6$-(2,6-Dimethylphenyl)-$N^2$-methyl-$N^2$-[2-(methylamino)ethyl]imidazo[1,5-a]pyrido[3,2-e]pyrazine-2,6-diamine;

N-(2-Chloro-6-methylphenyl)-2-(4-thiomorpholinyl)imidazo[1,5-a]pyrido[3,2-e]pyrazin-6-amine 1-oxide;

6-(2,6-Dimethylphenyl)-2-(4-thiomorpholinyl)imidazo[1,5-a]pyrido[3,2-e]pyrazin-6-amine 1-oxide;

4-[6-[(2-Chloro-6-methylphenyl)amino]imidazo[1,5-a]pyrido[3,2-e]pyrazin-2-yl]-2-piperazineethanol;

4-[6-[(2,6-Dimethylphenyl)amino]imidazo[1,5-a]pyrido[3,2-e]pyrazin-2-yl]-2-piperazineethanol;

3-[[6-[(2,6-Dimethylphenyl)amino]imidazo[1,5-a]pyrido[3,2-e]pyrazin-2-yl]methylamino]-1,2-propanediol;

$N^6$-(2-Chloro-6-methylphenyl)-$N^2$-(2,2-dimethoxyethyl)imidazo[1,5-a]pyrido[3,2-e]pyrazine-2,6-diamine;

(R)-3-[4-[6-[(2-Chloro-6-methylphenyl)amino]imidazo[1,5-a]pyrido[3,2-e]pyrazin-2-yl]-1-piperazinyl]-1,2-propanediol;

(R)-3-[4-[6-[(2-Dimethylphenyl)amino]imidazo[1,5-a]pyrido[3,2-e]pyrazin-2-yl]-1-piperazinyl]-1,2-propanediol;

(S)-4-[6-[(2-Chloro-6-methylphenyl)amino]imidazo[1,5-a]pyrido[3,2-e]pyrazin-2-yl]-1-piperazinyl]-1,2-piperazinemethanol;

(S)-4-[6-[(2,6-Dimethylphenyl)amino]imidazo[1,5-a]pyrido[3,2-e]pyrazin-2-yl]-2-piperazinemethanol;

(R)-4-[6-[(2-Chloro-6-methylphenyl)amino]imidazo[1,5-a]pyrido[3,2-e]pyrazin-2-yl]-2-piperazinemethanol;

(R)-4-[6-[(2,6-Dimethylphenyl)amino]imidazo[1,5-a]pyrido[3,2-e]pyrazin-2-yl]-2-piperazinemethanol;

trans-N-(2-Chloro-6-methylphenyl)-2-(2,5-dimethyl-1-piperazinyl)imidazo[1,5-a]pyrido[3,2-e]pyrazin-6-amine;

N-(2-Chloro-6-methylphenyl)-7-(1-piperazinyl)imidazo[1,5-a]pyrido[4,3-e]pyrazin-4-amine;

$N^4$-(2-Chloro-6-methylphenyl)-$N^7$-[2-(dimethylamino)ethyl]imidazo[1,5-a]pyrido[4,3-e]pyrazine-4,7-diamine;

$N^4$-(2-Chloro-6-methylphenyl)-$N^7$-[2-(4-morpholinyl)ethyl]imidazo[1,5-a]pyrido[4,3-e]pyrazine-4,7-diamine;

(S)-N-(2-Chloro-6-methylphenyl)-8-(3-methyl-1-piperazinyl)imidazo[1,5-a]pyrido[3,4-e]pyrazin-4-amine;

cis-N-(2-Chloro-6-methylphenyl)-8-(3,5-dimethyl-1-piperazinyl)imidazo[1,5-a]pyrido[3,4-e]pyrazin-4-amine;

N-Butyl-N'-[6-[(2,6-dimethylphenyl)amino]imidazo[1,5-a]pyrido[3,2-e]pyrazin-9-yl]urea;

N-[6-[(2,6-Dimethylphenyl)amino]imidazo[1,5-a]pyrido[3,2-e]pyrazin-9-yl]-N'-(phenylmethyl)urea;

N-[6-[(2,6-Dimethylphenyl)amino]imidazo[1,5-a]pyrido[3,2-e]pyrazin-9-yl]-N'-propylurea;

N-[6-[(2,6-Dimethylphenyl)amino]imidazo[1,5-a]pyrido[3,2-e]pyrazin-9-yl]-N'-(1-methylethyl)urea.

10. A method for the treatment of a protein tyrosine kinase-associated disorder, comprising the step of administering to a subject in need thereof an amount effective therefor of at least one compound of claim 1.

11. The method of claim 10, wherein said protein tyrosine kinase-associated disorder is transplant rejection.

12. The method of claim 10, wherein said protein tyrosine kinase-associated disorder is rheumatoid arthritis.

13. The method of claim 10, wherein said protein tyrosine kinase-associated disorder is multiple sclerosis.

14. The method of claim 10, wherein said protein tyrosine kinase-associated disorder is inflammatory bowel disease.

15. The method of claim 10, wherein said protein tyrosine kinase-associated disorder is lupus.

16. The method of claim 10, wherein said protein tyrosine kinase-associated disorder is graft vs. host disease.

17. The method of claim 10, wherein said protein tyrosine kinase-associated disorder is a T-cell mediated hypersensitivity disease.

18. The method of claim 10, wherein said protein tyrosine kinase-associated disorder is psoriasis.

19. The method of claim 10, wherein said protein tyrosine kinase-associated disorder is Hashimoto's thyroiditis.

20. The method of claim 10, wherein said protein tyrosine kinase-associated disorder is Guillain-Barre syndrome.

21. The method of claim 10, wherein said protein tyrosine kinase-associated disorder is chronic obstructive pulmonary disorder.

22. The method of claim 10, wherein said protein tyrosine kinase-associated disorder is a cancer where a Src-family kinase is activated or overexpressed or where Src-family kinase activity facilitates tumor growth or survival.

23. The method of claim 10, wherein said protein tyrosine kinase-associated disorder is contact dermatitis.

24. The method of claim 10, wherein said protein tyrosine kinase-associated disorder is an allergic disease.

25. The method of claim 10, wherein said protein tyrosine kinase-associated disorder is asthma.

26. The method of claim 10, wherein said protein tyrosine kinase-associated disorder is ischemic or reperfusion injury.

27. The method of claim 10, wherein said protein tyrosine kinase-associated disorder is atopic dermatitis.

28. The method of claim 10, wherein said protein tyrosine kinase-associated disorder is allergic rhinitis.

29. The method of claim 10, wherein said protein tyrosine kinase is Lck.

30. The method of claim 10, wherein said protein tyrosine kinase is Fyn.

31. The method of claim 10, wherein said protein tyrosine kinase is Lyn.

32. The method of claim 10, wherein said protein tyrosine kinase is Hck.

33. The method of claim 10, wherein said protein tyrosine kinase is Fgr.

34. The method of claim 10, wherein said protein tyrosine kinase is Scr.

35. The method of claim 10, wherein said protein tyrosine kinase is Blk.

36. The method of claim 10, wherein said protein tyrosine kinase is Yes.

37. The method of claim 10, wherein said compound of the formula I or salt thereof is administered, simultaneously or sequentially, with an antiinflammatory, antiproliferative, chemotherapeutic agent, immunosuppressant or PTK inhibitor other than a compound of the formula I or salt thereof.

38. The method of claim 27, wherein said compound of the formula I or salt thereof is administered with one or more of: another PTK inhibitor; cyclosporin A; CTLA4-Ig; antibodies selected from anti-ICAM-3, anti-IL-2 receptor (Anti-Tac), anti-CD45RB, anti-CD2, anti-CD3 (OKT-3), anti-CD4, anti-CD80, anti-CD86, and monoclonal antibody OKT3; agents blocking the interaction between CD40 and gp39; fusion proteins constructed from DC40 and gp39; inhibitors of NF-kappa B function; non-steroidal antiinflammatory drugs (NSAIDs); steroids; gold compounds; antiproliferative agents; FK506 (tacrolimus, Prograf); mycophenolate mofetil; cytotoxic drugs; TNF-α inhibitors; anti-TNF antibodies or soluble TNF receptor; rapamycin (sirolimus or Rapamune); leflunimide (Arava); and cyclooxygenase-2 inhibitors; or derivatives thereof.

39. A method for the treatment of a T cell mediated disorder, comprising the step of administering to a subject in need thereof an amount effective therefor of at least one compound of claim 1.

40. The method of claim 39, wherein T cell activation is inhibited.

41. A pharmaceutical composition for the treatment of a protein kinase-associated disorder, comprising a pharmaceutically acceptable vehicle or diluent and at least one compound of the formula I or pharmaceutically acceptable salt thereof of claim 1 in an amount effective therefor.

42. A method for the preparation of a compound of the following formula 9 or salt thereof:

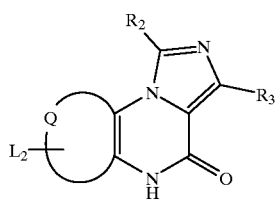

9 where
Q, together with the atoms to which it is bonded, forms a 5-, 6- or 7-membered heterocyclic ring;
$L_2$ represents one or more optionally present leaving groups;
$R_2$ and $R_3$ are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —$OR_6$;
(3) —SH or —$SR_7$;
(4) —$C(O)_qH$, —$C(O)_qR_6$, or —O—$C(O)_qR_6$, where q is 1 or 2;
(5) —$SO_3H$ or —$S(O)_qr_6$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$SiR_{13}R_{14}R_{15}$; or
(13) —$P(O)(OR_6)_2$;
$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;
$R_{13}$, $R_{14}$ and $R_{15}$ are each independently:

(1) alkyl; or
(2) phenyl;
$Z_1$, $Z_2$ and $Z_3$ are each independently:
(1) hydrogen of $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more or the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$;
(5) —$SO_3H$ or —$S(O)_qZ_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$—$Z_6$;
(12) —$Z_4$-13 $N(Z_{10})$—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_1$—O—;
$Z_4$ and $Z_5$ are each independently:
(1) a single bond;
(2) —$Z_{11}$—$S(O)_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—; or
(8) —$Z_{11}$—C(O)—O—$Z_{12}$—;
$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$ together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and
$Z_{11}$ and $Z_{12}$ are each independently:
(1) a single bond;
(2) alkylene;
(3) alkenylene; or
(4) alkynylene;
comprising the step of contacting a compound of the following formula 16 or salt thereof:

101
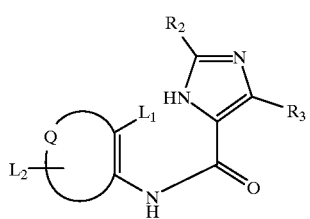
102
where $L_1$ is a leaving group, and Q, $L_2$, and $R_3$ are as defined above; with a base, wherein a copper I salt is optionally employed with said base.
* * * * *

UNITED STATES PATENT AND TRADEMARK OFFICE
CERTIFICATE OF CORRECTION

PATENT NO. : 5,990,109
DATED : November 23, 1999
INVENTOR(S) : Ping Chen et al.

It is certified that error appears in the above-identified patent and that said Letters Patent is hereby corrected as shown below:

<u>Title page,</u>
Item [75], the inventors should be as following:

-- Ping Chen, Lawrenceville; Derek J. Norris, Trenton, both of N.J.; Joel C. Barrish, Holland, Pa.; Edwin J. Iwanowicz, Cranbury, N.J.; Henry H. Gu, Morrisville, Pa; Gary L. Schieven, Lawrenceville, N.J. --

Signed and Sealed this

First Day of July, 2003

JAMES E. ROGAN
*Director of the United States Patent and Trademark Office*